United States Patent
Chen et al.

(10) Patent No.: US 11,390,677 B2
(45) Date of Patent: Jul. 19, 2022

(54) HUMAN ANTI-CD47 ANTIBODIES AND USES THEREOF

(71) Applicant: Trican Biotechnology Co., Ltd, New Taipei (TW)

(72) Inventors: Huang-Tsu Chen, Cupertino, CA (US); Jiun-Shyang Leou, Hsinchu (TW); Chung-Yuan Hsu, Kaohsiung (TW); Cheng-Ke Li, Taoyuan (TW); Yun-Ting Wang, New Taipei (TW); Li-Tsen Lin, New Taipei (TW); Shiou-Ting Chen, New Taipei (TW); Chen-Wei Chiang, Taipei (TW)

(73) Assignee: TRICAN BIOTECHNOLOGY CO., LTD., New Taipei (TW)

( * ) Notice: Subject to any disclaimer, the term of this patent is extended or adjusted under 35 U.S.C. 154(b) by 253 days.

(21) Appl. No.: 16/502,751

(22) Filed: Jul. 3, 2019

(65) Prior Publication Data

US 2020/0010546 A1    Jan. 9, 2020

Related U.S. Application Data

(60) Provisional application No. 62/694,172, filed on Jul. 5, 2018.

(51) Int. Cl.
| C07K 16/28 | (2006.01) |
| A61P 35/00 | (2006.01) |
| A61K 39/00 | (2006.01) |

(52) U.S. Cl.
CPC .......... *C07K 16/2803* (2013.01); *A61P 35/00* (2018.01); *A61K 2039/505* (2013.01); *C07K 2317/55* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 9,017,675 | B2 * | 4/2015 | Liu | G01N 33/6872 |
| | | | | 424/133.1 |
| 9,045,541 | B2 * | 6/2015 | Eckelman | C07K 16/2803 |
| 9,650,441 | B2 * | 5/2017 | Grosveld | C07K 16/2896 |
| 10,035,855 | B2 * | 7/2018 | Swanson | A61P 11/06 |
| 10,844,124 | B2 * | 11/2020 | Manning | A61P 17/06 |
| 11,014,984 | B2 * | 5/2021 | Gong | C07K 16/2803 |

OTHER PUBLICATIONS

Konitzer et al., PLoS ONE, 10(12):e0145633, doi:10.1371/journal.pone.0145633, 2015.*

* cited by examiner

*Primary Examiner* — Marianne P Allen
(74) *Attorney, Agent, or Firm* — Birch, Stewart, Kolasch & Birch, LLP

(57) ABSTRACT

The present invention provides antibodies that bind to CD47 with high affinity and specificity, and their use in treatment of a cancer.

6 Claims, 13 Drawing Sheets

Specification includes a Sequence Listing.

SEQUENCE LISTING

```
<160> NUMBER OF SEQ ID NOS: 21

<210> SEQ ID NO 1
<211> LENGTH: 122
<212> TYPE: PRT
<213> ORGANISM: Homo sapiens

<400> SEQUENCE: 1

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Arg
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Leu Ile Thr Phe Gly Gly Arg Arg Ala Phe Asp Ile Trp
            100                 105                 110

Gly Gln Gly Thr Met Val Thr Val Ser Ser
        115                 120

<210> SEQ ID NO 2
<211> LENGTH: 216
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Tyr Thr Phe Gly Gln Gly Thr Lys Leu Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 3
<211> LENGTH: 121
<212> TYPE: PRT
<213> ORGANISM: Homo sapiens

<400> SEQUENCE: 3

Gln Val Thr Leu Lys Glu Ser Gly Pro Thr Leu Val Lys Pro Thr Gln
 1               5                  10                  15

Thr Leu Thr Leu Thr Cys Thr Phe Ser Gly Leu Ser Leu Ser Thr Ser
             20                  25                  30

Gly Val Gly Val Gly Trp Ile Arg Gln Pro Pro Gly Lys Ala Leu Trp
         35                  40                  45

Leu Ala Leu Ile Tyr Trp Asn Asp Asp Lys Arg Tyr Ser Pro Ser Leu
 50                  55                  60

Lys Ser Arg Leu Thr Val Thr Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala His Leu Ile Thr Phe Gly Gly Arg Arg Ala Phe Asp Ile Trp Gly
                100                 105                 110

Gln Gly Thr Met Val Thr Val Ser Ser
            115                 120

<210> SEQ ID NO 4
<211> LENGTH: 215
<212> TYPE: PRT
<213> ORGANISM: Homo sapiens
```

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Arg Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 121
<212> TYPE: PRT
<213> ORGANISM: Homo sapiens

<400> SEQUENCE: 5

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Phe Gly Pro Ser Arg Ser Ser Ala Phe Asp Ile Trp Gly
            100                 105                 110

Gln Gly Thr Met Val Thr Val Ser Ser
        115                 120
```

<210> SEQ ID NO 6
<211> LENGTH: 218
<212> TYPE: PRT
<213> ORGANISM: Homo sapiens

<400> SEQUENCE: 6

Asn Phe Met Leu Thr Gln Pro Pro Ser Val Ser Gly Ala Pro Gly Gln
1               5                   10                  15

Ser Val Thr Ile Ser Cys Thr Gly Thr Tyr Ser Asn Ile Gly Arg Asn
            20                  25                  30

Tyr Val Thr Trp Tyr Gln Gln Phe Pro Gly Thr Ala Pro Lys Leu Leu
        35                  40                  45

Val Gln Trp Asn Asn Arg Arg Pro Ser Gly Ile Pro Asp Arg Phe Ser
    50                  55                  60

Ala Ser Arg Ser Arg Ser Asp Ala Ser Ala Ser Leu Ala Ile Ser Gly
65                  70                  75                  80

Val Arg Ser Glu Asp Glu Ala Asp Tyr Tyr Cys Ala Ala Trp Asp Asp
                85                  90                  95

Ser Leu Ser Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Ala Glu Cys Ser
    210                 215

<210> SEQ ID NO 7
<211> LENGTH: 120
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Arg Trp Leu His Arg Val Phe Asp Tyr Trp Gly Gln
            100                 105                 110

Gly Thr Thr Val Thr Val Ser Ser
        115                 120

<210> SEQ ID NO 8
<211> LENGTH: 217
<212> TYPE: PRT
<213> ORGANISM: Homo sapiens

<400> SEQUENCE: 8

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Ile Ile Phe Asp Val Ile Asn Arg Pro Ser Gly Val Ser Ser Arg Phe
    50                  55                  60

Ser Gly Ser Lys Ser Gly Thr Ser Ala Thr Leu Val Ile Thr Gly Leu
65                  70                  75                  80

Gln Thr Gly Asp Glu Ala Asp Tyr Tyr Cys Gly Thr Trp Asp Asn Ser
                85                  90                  95

Leu Arg Ala Tyr Val Phe Gly Ser Gly Thr Asn Val Thr Ala Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Ala Glu Cys Ser
    210                 215

<210> SEQ ID NO 9
<211> LENGTH: 117
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Arg Leu Ser Cys Lys Ala Ser Gly Tyr Thr Phe Ser Ser Tyr
            20                  25                  30

Tyr Met His Trp Val Arg Gln Ala Pro Gly Gln Gly Leu Val Trp Met
        35                  40                  45

Gly Thr Ser Ile Pro Thr Ala Ala Ser Gly Ser Tyr Ala Gln Lys Phe
    50                  55                  60

Gln Gly Arg Val Thr Met Thr Arg Asp Thr Ser Thr Thr Thr Val Tyr
65                  70                  75                  80

```
Met Glu Leu Ser Ser Leu Arg Ser Glu Asp Thr Ala Val Tyr Tyr Cys
                    85                  90                  95

Ala Arg Gly Gly Arg Gly Gly Phe Asp Tyr Trp Gly Gln Gly Thr Pro
                100                 105                 110

Val Thr Val Ser Ser
            115

<210> SEQ ID NO 10
<211> LENGTH: 216
<212> TYPE: PRT
<213> ORGANISM: Homo sapiens

<400> SEQUENCE: 10

Gln Pro Gly Leu Thr Gln Pro Pro Ser Val Ser Lys Gly Leu Arg Arg
1               5                   10                  15

Thr Ala Thr Leu Thr Cys Thr Gly Asn Ser Asn Asn Val Gly Asn Gln
                20                  25                  30

Gly Ala Val Trp Leu Gln Gln His Gln Gly His Pro Pro Lys Leu Leu
            35                  40                  45

Ser Tyr Arg Asn Asn Asn Arg Pro Ser Gly Ile Ser Glu Arg Phe Ser
    50                  55                  60

Ala Ser Arg Ser Ala Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Gly Trp Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Lys Ser Tyr Ser Cys Gln Val Thr His Asp Gly Ser Thr Val Glu Lys
            195                 200                 205

Thr Val Ala Pro Ala Glu Cys Ser
    210                 215

<210> SEQ ID NO 11
<211> LENGTH: 117
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Gly Thr Leu Gly Met Asp Val Trp Gly Gln Gly Thr Thr
        100                 105                 110

Val Thr Val Ser Ser
        115

<210> SEQ ID NO 12
<211> LENGTH: 214
<212> TYPE: PRT
<213> ORGANISM: Homo sapiens

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
            85                  90                  95

Tyr Val Phe Gly Thr Gly Thr Lys Val Thr Val Leu Gly Gln Pro Lys
        100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 13
<211> LENGTH: 119
<212> TYPE: PRT
<213> ORGANISM: Homo sapiens

<400> SEQUENCE: 13

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Thr Tyr
            20                  25                  30

His Ile His Trp Val Arg Gln Ala Pro Gly Gln Gly Leu Glu Trp Met
        35                  40                  45

Gly Val Ile Asn Ser Asn Ala Gly Asn Thr Gly Tyr Ala Gln Asn Phe
         50                  55                  60

Gln Asp Arg Val Thr Met Thr Arg Asp Thr Ser Thr Ser Thr Val Tyr
 65                  70                  75                  80

Met Glu Leu Arg Ser Leu Lys Ser Asp Asp Thr Ala Val Tyr Tyr Cys
                 85                  90                  95

Ala Lys Asp Pro Gly Met Gly Trp Tyr Met His His Trp Gly Gln Gly
                100                 105                 110

Thr Leu Val Thr Val Ser Ser
            115

<210> SEQ ID NO 14
<211> LENGTH: 216
<212> TYPE: PRT
<213> ORGANISM: Homo sapiens

<400> SEQUENCE: 14

Asn Phe Met Leu Thr Gln Pro Gln Ser Val Ser Gly Ser Pro Gly Glu
 1               5                  10                  15

Thr Val Thr Ile Ser Cys Thr Gly Ser Gly Gly Pro Ile Ala Ser Asn
                20                  25                  30

Tyr Val Gln Trp Tyr Gln Gln Arg Pro Gly Ser Val Pro Thr Thr Val
             35                  40                  45

Ile Tyr Glu Asp Thr Lys Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Glu Ser
                 85                  90                  95

Arg Asn Tyr Val Phe Gly Thr Gly Thr Lys Val Ser Val Leu Ser Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 15
<211> LENGTH: 449
<212> TYPE: PRT
<213> ORGANISM: Homo sapiens

<400> SEQUENCE: 15

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Arg
                20                  25                  30

Gly Val Gly Val Gly Trp Ile Arg Gln Pro Pro Gly Lys Ala Leu Glu
    35                  40                  45

Trp Leu Ala Leu Ile Tyr Trp Asn Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Leu Ile Thr Phe Gly Gly Arg Arg Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 16
<211> LENGTH: 449
<212> TYPE: PRT
<213> ORGANISM: Homo sapiens

<400> SEQUENCE: 16

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Leu Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Leu Ile Thr Phe Gly Gly Arg Arg Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380
```

-continued

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 17
<211> LENGTH: 448
<212> TYPE: PRT
<213> ORGANISM: Homo sapiens

<400> SEQUENCE: 17

Gln Met Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65              70                  75                  80

Leu Gln Trp Ser Ser Leu Lys Ala Ser Asp Thr Ala Met Tyr Tyr Cys
            85                  90                  95

Ala Arg Leu Phe Gly Pro Ser Arg Ser Ser Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

-continued

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 18
<211> LENGTH: 447
<212> TYPE: PRT
<213> ORGANISM: Homo sapiens

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Arg Trp Leu His Arg Val Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

-continued

```
Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
        260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 19
<211> LENGTH: 444
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Arg Leu Ser Cys Lys Ala Ser Gly Tyr Thr Phe Ser Ser Tyr
            20                  25                  30

Tyr Met His Trp Val Arg Gln Ala Pro Gly Gln Gly Leu Val Trp Met
        35                  40                  45

Gly Thr Ser Ile Pro Thr Ala Ala Ser Gly Ser Tyr Ala Gln Lys Phe
    50                  55                  60

Gln Gly Arg Val Thr Met Thr Arg Asp Thr Ser Thr Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Gly Phe Asp Tyr Trp Gly Gln Gly Thr Pro
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

-continued

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys
        435                 440

<210> SEQ ID NO 20
<211> LENGTH: 444
<212> TYPE: PRT
<213> ORGANISM: Homo sapiens

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Gly Thr Leu Gly Met Asp Val Trp Gly Gln Gly Thr Thr
        100                 105                 110

```
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 21
<211> LENGTH: 446
<212> TYPE: PRT
<213> ORGANISM: Homo sapiens

<400> SEQUENCE: 21

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Thr Tyr
            20                  25                  30

His Ile His Trp Val Arg Gln Ala Pro Gly Gln Gly Leu Glu Trp Met
        35                  40                  45
```

```
Gly Val Ile Asn Ser Asn Ala Gly Asn Thr Gly Tyr Ala Gln Asn Phe
        50                  55                  60

Gln Asp Arg Val Thr Met Thr Arg Asp Thr Ser Thr Ser Thr Val Tyr
 65                  70                  75                  80

Met Glu Leu Arg Ser Leu Lys Ser Asp Asp Thr Ala Val Tyr Tyr Cys
                 85                  90                  95

Ala Lys Asp Pro Gly Met Gly Trp Tyr Met His His Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

HUMAN ANTI-CD47 ANTIBODIES AND USES THEREOF

CROSS REFERENCE TO RELATED APPLICATIONS

This non-provisional application claims the benefit under 35 U.S.C. § 119(e) to U.S. Provisional Application No. 62/694,172, filed on Jul. 5, 2018, which is hereby expressly incorporated by reference into the present application.

FIELD OF THE INVENTION

The present invention pertains to anti-CD47 antibodies.

BACKGROUND OF THE INVENTION

CD47, a cell membrane protein, belongs to the immunoglobulin superfamily containing an extracellular N-terminal Ig variable (IgV) domain with five transmembrane domains and a short C-terminal intracellular tail. Four alternatively spliced isoforms of CD47 differ in the length of their cytoplasmic tails have been identified so far [Brown, E. (2001) *J Clin Invest* 107(12):1499-500; Reinhold, M. I., et al. (1995) *J Cell Sci* 108 (*Part 1*43419-25]. Recent studies demonstrated CD47 is a ligand of SIRP-α expressed on the phagocytic cells of immune system including macrophages, dendritic cells, and neutrophils [Tsai et al. (2008) *J Cell Biol* 180(5):989-1003]. The CD47-SIRP-α interactive axis has been shown to be involved in several cellular processes including apoptosis [Wang et al. (2016) *J Dent Res* 95(6): 697-703], proliferation [Sick et al. (2011) Glia 59(2):308-19; Kaur et al. (2013) *Sci Rep* 3:1673], adhesion, and migration [Rebres et al. (2005) *J Cell Physiol* 205(2):182-93; Sick et al. (2012) *Br J Pharmacol* 167(7):1415-30]. Additionally, studies also suggested CD47-SIRP-α interaction plays important role angiogenic processes as well [Zhang et al. (2015) *Brain Res* 1623:74-80; Chao et al. (2012) *Curr Opin Immunol* 24(2): 225-32].

CD47 is ubiquitously expressed by all human cells and has been shown to be over-expressed in various tumor cells. Indeed, most human cancers studied to date, including acute myeloid leukemia (AML), chronic myeloid leukemia [Jaiswal et al. (2009) *Cell* 138(2):271-85], acute lymphoblastic leukemia (ALL) [Chao et al. (2011) *Cancer Res* 71(4):1374-84], non-Hodgkin's lymphoma (NHL) [Chao et al. (2010) *Cell* 142(5):699-713], multiple myeloma (MM) [Rendtlew et al. (2007) *Br J Haematol* 138(6):756-60], bladder cancer, and other solid tumors (Chan et al. (2009) *Proc Natl Acad Sci USA* 106(33):14016-21), overexpress surface CD47, making CD47 an universal target to treat human cancers. High levels of CD47 were shown to allow cancer cells to avoid phagocytosis due to engage of the SIRP-α on phagocytes with CD47. The interaction between CD47 and SIRP-α, provides a "don't-eat-me" signal to phagocytes and prevents the phagocytic elimination of cancer cells and inhibits the T-cell immune response, subsequently [Oldenborg et al. (2000) *Science* 288(5473):2051-4, Blazar et al. (2001) *J Exp Med* 194(4): 541-9. ]Since tumor cells overexpress CD47 to escape surveillance of host immune system, CD-47 targeted therapy aiming to restore the clearance of tumor cells were actively tested in clinical currently.

A number of therapeutics targeting the CD47-SIRP-α axis is currently under-developing including anti-CD47 antibodies, engineered decoy receptor, anti-SIRP-α antibodies, and bispecific agents. Upon administration, anti-CD47 antibody or derivatives selectively inhibits the interaction between CD47 and SIRP-α. The blockage of CD47-SIRP-α interaction abrogates SIRP-α mediated inhibitory signals to phagocytes and results in, for example, macrophage activation and phagocytosis of tumor cells [Chao et al. (2011) *Cancer Res* 71(4):1374-84; Chao et al. (2010) *Cell* 142(5):699-713; Majeti et al. (2009) *Cell* 138(2): 286-99, Chao et al. (2010) *Sci Transl Med* 2(63):63ra94]. Furthermore, blocking CD47 transmitted signaling with antibodies also activates both an anti-tumor T-lymphocyte immune response and T cell-mediated killing of CD47-expressing tumor cells [Matozaki et al (2009) *Trends Cell Biol* 19(2):72-80; Latour et al. (2001) *J Immunol* 167(5):2547-54].

BRIEF SUMMARY OF THE INVENTION

Accordingly, the present invention provides new human CD47 blocking antibodies identified from a cancer patient antibody Fab library, hereinafter called as the anti-CD47 antibodies.

In one aspect, the present invention provides an isolated human anti-CD47 antibody, or an antigen-binding fragment thereof, comprising (a) a heavy chain variable (Vh) region comprises an amino acid sequence selected from the group consisting of SEQ ID NOs: 1, 3, 5, 7, 9, 11, and 13; (b) an L chain region having an amino acid sequence selected from the group consisting of SEQ ID NOs: 2, 4, 6, 8, 10, 12, and 14; or (c) a reformatted H chain region having an amino acid sequence selected from the group consisting of SEQ ID NOs: 15, 16, 17, 18, 19, 20, and 21.

In one example of the invention, the antibody or antigen-binding fragment thereof blocks the interaction of CD47 with signal-regulatory protein alpha (SIRP-α).

In another aspect, the invention provides IgG4-reformatted CD47 antibodies, which are prepared and obtained from the anti-CD47 antibodies.

In one example of the invention, the IgG4-reformatted CD47 blocking antibody were confirmed to be effective in treatment of a cancer since it is found in the invention that the IgG4-reformatted CD47 blocking antibody treated cancer cells, such as Jurkat-1 or HL60 cells, and induced robust phagocytosis activity explicated by polarized THP-1 macrophages as well as peripheral blood mononuclear cell (PBMC), but not antibody-dependent cell-mediated cytotoxicity (ADCC) and apoptosis of tested cancer cells, in vitro.

In one yet aspect, the present invention provides a method for treating a cancer, comprising administering to a subject in need thereof a therapeutically effective amount of the anti-CD47 antibodies.

In one embodiment, the broad spectrum of mammalian cancers to be treated is selected from the group consisting of acute myeloid leukemia, chronic myeloid leukemia, acute lymphoblastic leukemia, non-Hodgkin's lymphoma, multiple myeloma, bladder cancer, breast cancer, head-and-neck squamous cell carcinoma, ovarian cancer, and colon cancer.

In one further aspect, the present invention provides a pharmaceutical composition comprising a therapeutically acceptable amount of the anti-CD47 antibodies and one or more pharmaceutically acceptable carriers. In particular, the pharmaceutical composition is effective in the treatment of a cancer.

In the examples of the present invention, the anti-CD47 antibody comprises a heavy chain variable (Vh) region having an amino acid sequence selected from the group consisting of SEQ ID NOs: 1, 3, 5, 7, 9, 11, and 13.

In the examples of the present invention, the anti-CD47 antibody comprises a light chain region having an amino acid sequence selected from the group consisting of SEQ ID NOs: 2, 4, 6, 8, 10, 12, and 14.

In the examples of the present invention, the anti-CD47 antibody comprises a heavy chain region having an amino acid sequence selected from the group consisting of SEQ ID NOs: 15, 16, 17, 18, 19, 20, and 21.

In one yet aspect, the present invention provides a fragment binding to CD47, including a Fab, Fab', F(ab)$_2$, F(ab')2 or scFv of the antibody according the prevent invention.

BRIEF DESCRIPTION OF THE SEVERAL VIEWS OF THE DRAWINGS

FIG. 2A shows the results of the direct ELISA binding assay of purified antibodies against CD47-Fc protein; wherein the purified antibodies and Hu5F9-G4 were shown to bind, specifically, to CD47-Fc protein, but not to SIRP-α. FIG. 2B shows the titration ELISA analysis of purified antibodies against CD47-Fc protein; wherein the purified antibodies and Hu5F9-G4 were shown to bind recombinant CD47 in a dose-dependent manner with variable binding activities among purified CD47 antibodies.

DETAILED DESCRIPTION OF THE INVENTION

Figure 1:
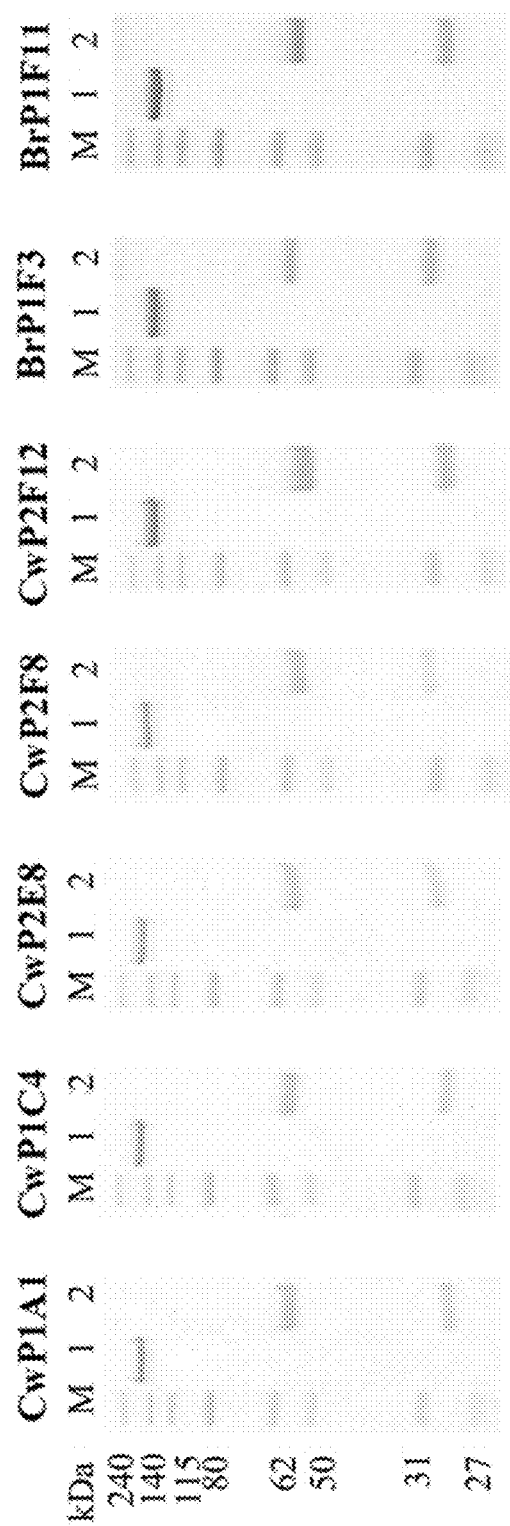
FIG. 1 shows the gel analysis of purified IgG4-reformatted CD47 antibodies; wherein the transiently HEK293F-expressed CD47 antibodies were purified from culture supernatant using Protein-G chromatography and purified antibody (~2 μg/lane) was PAGE-gel analyzed under reducing and non-reducing condition and visualized using Coomassie blue staining (M: Protein molecular weight marker; 1: CD47 antibody under non-reducing condition; 2: CD47 antibodies under reducing condition).

Unless defined otherwise, all technical and scientific terms used herein have the same meaning as commonly understood to one of ordinary skill in the art to which this invention pertains.

As used herein, the term "antibody" refers to immunoglobulin molecules comprised of four polypeptide chains, including two heavy (H) chains and two light (L) chains inter-connected by disulfide bonds. Antibodies may include intact immunoglobulins and the variants and portions of antibodies well known in the art. In the present invention, a fragment binding to CD47 is provided, including a Fab, Fab', F(ab)$_2$, F(ab')2 or scFv of the antibody according the prevent invention.

As used herein, the term "Fc" is the tail region of an antibody that interacts with cell surface receptors. This property allows antibodies to activate the immune system. In contrast to Fab, the Fc regions of all antibodies in a class are the same for each species; they are constant rather than variable.

As used herein, the term "Fragment antigen-binding" or "Fab" refers to an antigen-binding fragment on an antibody which binds to antigens. The Fab fragment is an antibody structure that still binds to antigens but is monovalent with no Fc portion. Fab is composed of one constant and one variable domain of each of the heavy and the light chain, wherein the variable domain contains the antigen-binding site, comprising a set of complementarity determining regions, at the amino terminal end of the monomer. An antibody digested by the enzyme papain yields two Fab fragments of about 50 kDa each and an Fc fragment.

The term "F(ab')₂" as used herein refers to a fragment antibody that is generated by pepsin digestion of a whole IgG antibody to remove most of the Fc region while leaving intact some of the hinge region. The F(ab')₂ fragments have two antigen-binding F(ab) portions linked together by disulfide bonds, and therefore are divalent with a molecular weight of about 110 kDa.

As used herein, the term "single-chain variable fragment" or "scFv" refers to a fusion protein of the variable regions of the heavy and light chains of an antibody or an immunoglobulin, connected with a short linker peptide, such as a linker having 10 to 25 amino acids. This single-chain variable fragment retains the specificity of the original antibody, despite removal of the constant regions and the introduction of the linker.

As used herein, the term "antibody-dependent cell-mediated cytotoxicity (ADCC)" refers to an immune mechanism through which Fc receptor-bearing effector cells can recognize and kill antibody-coated target cells expressing tumor- or pathogen-derived antigens on their surface.

The present invention provides the anti-CD47 antibodies that specifically bind to human CD47 and block the interaction of CD47 with SIRP-α. According to analyses as shown in Example 8 and Example 9, the anti-CD47 antibodies of the invention are capable to enhance macrophage-mediated phagocytosis and do not induce apoptosis.

According to the invention, the anti-CD47 antibody binds specifically to human and mouse CD47.

According to the invention, the anti-CD47 antibody comprises a heavy chain variable (Vh) region having an amino acid sequence selected from the group consisting of SEQ ID NOs: 1, 3, 5, 7, 9, 11, and 13.

According to the invention, the anti-CD47 antibody comprises an L chain region having an amino acid sequence selected from the group consisting of SEQ ID NOs: 2, 4, 6, 8, 10, 12, and 14.

According to the invention, the anti-CD47 antibody is one containing the amino acids selected from the group consisting of:
a Vh region having an amino acid sequence of SEQ ID NO: 1, and an L chain region having an amino acid sequence of SEQ ID NO: 2;
a Vh region having an amino acid sequence of SEQ ID NO: 3, and an L chain region having an amino acid sequence of SEQ ID NO: 4;
a Vh region having an amino acid sequence of SEQ ID NO: 5, and an L chain region having an amino acid sequence of SEQ ID NO: 6;
a Vh region having an amino acid sequence of SEQ ID NO: 7, and an L chain region having an amino acid sequence of SEQ ID NO: 8;
a Vh region having an amino acid sequence of SEQ ID NO: 9, and an L chain region having an amino acid sequence of SEQ ID NO: 10;
a Vh region having an amino acid sequence of SEQ ID NO: 11, and an L chain region having an amino acid sequence of SEQ ID NO: 12; and
a Vh region having an amino acid sequence of SEQ ID NO: 13, and an L chain region having an amino acid sequence of SEQ ID NO: 14.

In addition, the anti-CD47 antibody of the present invention comprises a reformatted H chain having the amino acid sequence selected from the group consisting of SEQ ID NOs: 15, 16, 17, 18, 19, 20, and 21.

The amino acid sequences are listed in the following tables:

TABLE 1

Amino Acid Sequences of the anti-CD47 Fabs binders identified from library screening.

| Clone | Heavy chain | Light chain |
|---|---|---|
| CwP1A1 | SEQ ID NO: 1<br>QITLKESGPTLVKPTQTLTLTC<br>TFSG<br>FSLSTRGVGVGWIRQPPGKA<br>LEWL<br>ALIYWNDDKRYSPSLKSRLTI<br>TKDT<br>SKNQVVLTMTNMDPVDTAT<br>YYCA<br>HLITFGGRRAFDIWGQGTMV<br>TVSS | SEQ ID NO: 2<br>EIVLTQSPGTLSLSPGERATLSCRA<br>SQSVSSSYLAWYQQKPGQAPRLLI<br>YGASSRATGIPDRFSGSGSGTDFT<br>LTISRLEPEDFAVYYCQQYGSSPLY<br>TFGQGTKLEIKRTVAAPSVFIFPPS<br>DEQLKSGTASVVCLLNNFYPREA<br>KVQWKVDNALQSGNSQESVTEQ<br>DSKDSTYSLSSTLTLSKADYEKHK<br>LYACEVTHQGLSSPVTKSFNRGEC |
| CwP1C4 | SEQ ID NO: 3<br>QVTLKESGPTLVKPTQTLTLT<br>CTFSGLSLSTSGVGVGWIRQP<br>PGKALWLALIYWNDDKRYSP<br>SLKSRLTVTKDTSKNQVVLT<br>MTNMDPVDTATYYCAHLITF<br>GGRRAFDIWGQGTMVTVSS | SEQ ID NO: 4<br>EIVLTQSPGTLSLSPGERATLSCRA<br>SRSVSSSYLAWYQQKPGQAPRLLI<br>YGASSRATGIPDRFSGSGSGTDFT<br>LTISRLEPEDFAVYYCQQYGSSLW<br>TFGQGTKVEIKRTVAAPSVFIFPPS<br>DEQLKSGTASVVCLLNNFYPREA<br>KVQWKVDNALQSGNSQESVTEQ<br>DSKDSTYSLSSTLTLSKADYEKHK<br>VYACEVTHQGLSSPVTKSFNRGE<br>C |
| CwP2E8 | SEQ ID NO: 5<br>QMQLVQSGAEVKKPGESLKI<br>SCKGSGYSFTSYWIGWVRQ<br>MPGKGLEWMGITYPGDSDTR<br>YSPSFQGQVTISADKSISTAYL<br>QWSSLKASDTAMYYCARLF<br>GPSRSSAFDIWGQGTMVTVS<br>S | SEQ ID NO: 6<br>NFMLTQPPSVSGAPGQSVTISCTG<br>TYSNIGRNYVTWYQQFPGTAPKL<br>LVQWNNRRPSGIPDRFSASRSRSD<br>ASASLAISGVRSEDEADYYCAAW<br>DDSLSGWVFGGGTKLTVLGQPKA<br>APSVTLFPPSSEELQANKATLVCLI<br>SDFYPGAVTVAWKADSSPVKAGV<br>ETTTPSKQSNNKYAASSYLSLTPE<br>QWKSHKSYSCQVTHEGSTVEKTV<br>APAECS |

TABLE 1 -continued

Amino Acid Sequences of the anti-CD47 Fabs binders identified from library screening.

| Clone | Heavy chain | Light chain |
| --- | --- | --- |
| CwP2F8 | SEQ ID NO: 7<br>QVQLVQSGAEVKKPGSSVKV<br>SCKASGGTFSSYAISWVRQA<br>PGQGLEWMGRIIPILGIANYA<br>QKFQGRVTITADKSTSTAYM<br>ELSSLRSEDTAVYYCARSLR<br>WLHRVFDYWGQGTTVTVSS | SEQ ID NO: 8<br>QSVLTQPASVSGSPGQSITISCTGT<br>SSDVGGYNYVSWYQQHPGKAPK<br>LIIFDVINRPSGVSSRFSGSKSGTSA<br>TLVITGLQTGDEADYYCGTWDNS<br>LRAYVFGSGTNVTALGQPKANPT<br>VTLFPPSSEELQANKATLVCLISDF<br>YPGAVTVAWKADGSPVKAGVETT<br>KPSKQSNNKYAASSYLSLTPEQW<br>KSH<br>RSYSCQVTHEGSTVEKTVAPAECS |
| CwP2F12 | SEQ ID NO: 9<br>QVQLVQSGAEVKKPGASVRL<br>SCK<br>ASGYTFSSYYMHWVRQAPG<br>QGLVWMGTSIPTAASGSYAQ<br>KFQGRVTMTRDTSTTTVYME<br>LSSLRSEDTAVYYCARGGRG<br>GFDYWGQGTPVTVSS | SEQ ID NO: 10<br>QPGLTQPPSVSKGLRRTATLTCTG<br>NSNNVGNQGAVWLQQHQGHPPK<br>LLSYRNNNRPSGISERFSASRSAN<br>TASLTITGLQPEDEADYYCSAWDS<br>SLSGWVFGGGTKLTVLGQPKAAP<br>SVTLFPPSSEELQANKATLVCLISD<br>FYPGAVTVAWKADSSPVKAGVET<br>TTPSKQSNNKYAASSYLSLTPEQW<br>KSHKSYSCQVTHDGSTVEKTVAP<br>AECS |
| BrP1F3 | SEQ ID NO: 11<br>QVQLVQSGAEVKKPGASVK<br>VSCKASGYTFTSYYMHWVR<br>QAPGQGLEWMGIINPSGGST<br>SYAQKFQGRVTMTRDTSTST<br>VYMELSSLRSEDTAVYYCAR<br>GGTLGMDVWGQGTTVTVSS | SEQ ID NO: 12<br>SSELTQDPAVSVALGQTVRITCQG<br>DSLRSYYASWYQQKPGQAPVLVI<br>YGKNNRPSGIPDRFSGSSSGNTAS<br>LTITGAQAEDEADYYCNSRDSSG<br>NHYVFGTGTKVTVLGQPKANPTV<br>TLFPPSSEELQANKATLVCLISDFY<br>PGAVTVAWKADSSPVKAGVETTT<br>PSKQSNNKYAASSYLSLTPEQWKS<br>HRSYSCQVTHEGSTVEKTVAPTEC<br>S |
| BrP1F11 | SEQ ID NO: 13<br>QVQLVQSGAEVKKPGASVKI<br>SCKASGYTFTTYHIHWVRQA<br>PGQGLEWMGVINSNAGNTG<br>YAQNFQDRVTMTRDTSTSTV<br>YMELRSLKSDDTAVYYCAK<br>DPGMGWYMHHWGQGTLVT<br>VSS | SEQ ID NO: 14<br>NFMLTQPQSVSGSPGETVTISCTG<br>SGGPIASNYVQWYQQRPGSVPTT<br>VIYEDTKRPSGVPDRFSGSIDSSSN<br>SASLTISGLKTEDEADYYCQSYES<br>RNYVFGTGTKVSVLSQPKANPTV<br>TLFPPSSEELQANKATLVCLISDFY<br>PGAVTVAWKADGSPVKAGVETTK<br>PSKQSNNKYAASSYLSLTPEQWKS<br>HRSYSCQVTHEGSTVEKTVAPTEC<br>S |

TABLE 2

Amino Acid Sequences of the heavy chains of the IgG4-reformatted CD47 Antibodies.

| CwP1A1 | SEQ ID NO: 15<br>QITLKESGPTLVKPTQTLTLTCTFSGFSLSTRGVGVGWIRQPPGKAL<br>EWLALIYWNDDKRYSPSLKSRLTITKDTSKNQVVLTMTNMDPVDT<br>ATYYCAHLITFGGRRAFDIWGQGTMVTVSSASTKGPSVFPLAPCSR<br>STSESTAALGCLVKDYFPEPVTVSWNSGALTSGVHTFPAVLQSSGLY<br>SLSSVVTVPSSSLGTKTYTCNVDHKPSNTKVDKRVESKYGPPCPPC<br>PAPEFLGGPSVFLFPPKPKDTLMISRTPEVTCVVVDVSQEDPEVQFN<br>WYVDGVEVHNAKTKPREEQFNSTYRVVSVLTVLHQDWLNGKEY<br>KCKVSNKGLPSSIEKTISKAKGQPREPQVYTLPPSQEEMTKNQVSL<br>TCLVKGFYPSDIAVEWESNGQPENNYKTTPPVLDSDGSFFLYSRLT<br>VDKSRWQEGNVFSCSVMHEALHNHYTQKSLSLSLGK |
| --- | --- |

TABLE 2 -continued

Amino Acid Sequences of the heavy chains of the
IgG4-reformatted CD47 Antibodies.

CwP1C4   SEQ ID NO: 16
         QVTLKESGPTLVKPTQTLTLTCTFSGLSLSTSGVGVGWIRQPPGKAL
         EWLALIYWNDDKRYSPSLKSRLTVTKDTSKNQVVLTMTNMDPVD
         TATYYCAHLITFGGRRAFDIWGQGTMVTVSSASTKGPSVFPLAPCS
         RSTSESTAALGCLVKDYFPEPVTVSWNSGALTSGVHTFPAVLQSSG
         LYSLSSVVTVPSSSLGTKTYTCNVDHKPSNTKVDKRVESKYGPPCP
         PCPAPEFLGGPSVFLFPPKPKDTLMISRTPEVTCVVVDVSQEDPEVQ
         FNWYVDGVEVHNAKTKPREEQFNSTYRVVSVLTVLHQDWLNGKE
         YKCKVSNKGLPSSIEKTISKAKGQPREPQVYTLPPSQEEMTKNQVS
         LTCLVKGFYPSDIAVEWESNGQPENNYKTTPPVLDSDGSFFLYSRLT
         VDKSRWQEGNVFSCSVMHEALHNHYTQKSLSLSLGK

CwP2E8   SEQ ID NO: 17
         QMQLVQSGAEVKKPGESLKISCKGSYSFTSYWIGWVRQMPGKG
         LEWMGITYPGDSDTRYSPSFQGQVTISADKSISTAYLQWSSLKASDT
         AMYYCARLFGPSRSSAFDIWGQGTMVTVSSASTKGPSVFPLAPCS
         RSTSESTAALGCLVKDYFPEPVTVSWNSGALTSGVHTFPAVLQSSG
         LYSLSSVVTVPSSSLGTKTYTCNVDHKPSNTKVDKRVESKYGPPCP
         PCPAPEFLGGPSVFLFPPKPKDTLMISRTPEVTCVVVDVSQEDPEVQ
         FNWYVDGVEVHNAKTKPREEQFNSTYRVVSVLTVLHQDWLNGKE
         YKCKVSNKGLPSSIEKTISKAKGQPREPQVYTLPPSQEEMTKNQVS
         LTCLVKGFYPSDIAVEWESNGQPENNYKTTPPVLDSDGSFFLYSRLT
         VDKSRWQEGNVFSCSVMHEALHNHYTQKSLSLSLGK

CwP2F8   SEQ ID NO: 18
         QVQLVQSGAEVKKPGSSVKVSCKASGGTFSSYAISWVRQAPGQGL
         EWMGRIIPILGIANYAQKFQGRVTITADKSTSTAYMELSSLRSEDTA
         VYYCARSLRWLHRVFDYWGQGTTVTVSSASTKGPSVFPLAPCSRS
         TSESTAALGCLVKDYFPEPVTVSWNSGALTSGVHTFPAVLQSSGLYS
         LSSVVTVPSSSLGTKTYTCNVDHKPSNTKVDKRVESKYGPPCPPCP
         APEFLGGPSVFLFPPKPKDTLMISRTPEVTCVVVDVSQEDPEVQFN
         WYVDGVEVHNAKTKPREEQFNSTYRVVSVLTVLHQDWLNGKEY
         KCKVSNKGLPSSIEKTISKAKGQPREPQVYTLPPSQEEMTKNQVSL
         TCLVKGFYPSDIAVEWESNGQPENNYKTTPPVLDSDGSFFLYSRLT
         VDKSRWQEGNVFSCSVMHEALHNHYTQKSLSLSLGK

CwP2F12  SEQ ID NO: 19
         QVQLVQSGAEVKKPGASVRLSCK
         ASGYTFSSYYMHWVRQAPGQGLVWMGTSIPTAASGSYAQKFQGR
         VTM
         TRDTSTTTVYMELSSLRSEDTAVY
         YCARGGRGGFDYWGQGTPVTVSSASTKGPSVFPLAPCSRSTSESTA
         ALGCLVKDYFPEPVTVSWNSGALTSGVHTFPAVLQSSGLYSLSSVV
         TVPSSSLGTKTYTCNVDHKPSNTKVDKRVESKYGPPCPPCPAPEFL
         GGPSVFLFPPKPKDTLMISRTPEVTCVVVDVSQEDPEVQFNWYVD
         GVEVHNAKTKPREEQFNSTYRVVSVLTVLHQDWLNGKEYKCKVS
         NKGLPSSIEKTISKAKGQPREPQVYTLPPSQEEMTKNQVSLTCLVK
         GFYPSDIAVEWESNGQPENNYKTTPPVLDSDGSFFLYSRLTVDKSR
         WQEGNVFSCSVMHEALHNHYTQKSLSLSLGK

BrP1F3   SEQ ID NO: 20
         QVQLVQSGAEVKKPGASVKVSCKASGYTFTSYYMHWVRQAPGQ
         GLEWMGIINPSGGSTSYAQKFQGRVTMTRDTSTSTVYMELSSLRSE
         DTAVYYCARGGTLGMDVWGQGTTVTVSSASTKGPSVFPLAPCSRS
         TSESTAALGCLVKDYFPEPVTVSWNSGALTSGVHTFPAVLQSSGLYS
         LSSVVTVPSSSLGTKTYTCNVDHKPSNTKVDKRVESKYGPPCPPCP
         APEFLGGPSVFLFPPKPKDTLMISRTPEVTCVVVDVSQEDPEVQFN
         WYVDGVEVHNAKTKPREEQFNSTYRVVSVLTVLHQDWLNGKEY
         KCKVSNKGLPSSIEKTISKAKGQPREPQVYTLPPSQEEMTKNQVSL
         TCLVKGFYPSDIAVEWESNGQPENNYKTTPPVLDSDGSFFLYSRLT
         VDKSRWQEGNVFSCSVMHEALHNHYTQKSLSLSLGK

BrP1F11  SEQ ID NO: 21
         QVQLVQSGAEVKKPGASVKISCKASGYTFTTYHIHWVRQAPGQGL
         EWMGVINSNAGNTGYAQNFQDRVTMTRDTSTSTVYMELRSLKSD
         DTAVYYCAKDPGMGWYMHHWGQGTLVTVSSASTKGPSVFPLAPC
         SRSTSESTAALGCLVKDYFPEPVTVSWNSGALTSGVHTFPAVLQSSG
         LYSLSSVVTVPSSSLGTKTYTCNVDHKPSNTKVDKRVESKYGPPCP
         PCPAPEFLGGPSVFLFPPKPKDTLMISRTPEVTCVVVDVSQEDPEVQ
         FNWYVDGVEVHNAKTKPREEQFNSTYRVVSVLTVLHQDWLNGKE
         YKCKVSNKGLPSSIEKTISKAKGQPREPQVYTLPPSQEEMTKNQVS
         LTCLVKGFYPSDIAVEWESNGQPENNYKTTPPVLDSDGSFFLYSRLT
         VDKSRWQEGNVFSCSVMHEALHNHYTQKSLSLSLGK

According to the invention, the anti-CD47 antibody is one containing the amino acids selected from the group consisting of:

an H chain region having an amino acid sequence selected from the group consisting of SEQ ID NO: 15, and an L chain region having an amino acid sequence selected from the group consisting of SEQ ID NO: 2;

an H chain region having an amino acid sequence selected from the group consisting of SEQ ID NO: 16, and an L chain region having an amino acid sequence selected from the group consisting of SEQ ID NO: 4;

an H chain region having an amino acid sequence selected from the group consisting of SEQ ID NO: 17, and an L chain region having an amino acid sequence selected from the group consisting of SEQ ID NO: 6;

an H chain region having an amino acid sequence selected from the group consisting of SEQ ID NO: 18, and an L chain region having an amino acid sequence selected from the group consisting of SEQ ID NO: 8;

an H chain region having an amino acid sequence selected from the group consisting of SEQ ID NO: 19, and an L chain region having an amino acid sequence selected from the group consisting of SEQ ID NO: 10;

an H chain region having an amino acid sequence selected from the group consisting of SEQ ID NO: 20, and an L chain region having an amino acid sequence selected from the group consisting of SEQ ID NO: 12; and an H chain region having an amino acid sequence selected from the group consisting of SEQ ID NO: 21, and an L chain region having an amino acid sequence selected from the group consisting of SEQ ID NO: 14.

Throughout this document, reference is made to the following representative anti-CD47 antibodies of the invention. CwP1A1 represents an antibody having an H chain region corresponding to SEQ ID NO: 15, and an L chain region corresponding to SEQ ID NO: 2. CwP1C4 represents an antibody having an H chain region corresponding to SEQ ID NO: 16, and an L chain region corresponding to SEQ ID NO: 4. CwP2E8 represents an antibody having an H chain region corresponding to SEQ ID NO: 17, and an L chain region corresponding to SEQ ID NO: 6. CwP2F8 represents an antibody having an H chain region corresponding to SEQ ID NO: 18, and an L chain region corresponding to SEQ ID NO: 8. CwP2F12 represents an antibody having an H chain region corresponding to SEQ ID NO: 19, and an L chain region corresponding to SEQ ID NO: 10. BrP1F3 represents an antibody having an H chain region corresponding to SEQ ID NO: 20, and an L chain region corresponding to SEQ ID NO: 12. BrP1F11 represents an antibody having an H chain region corresponding to SEQ ID NO: 21, and an L chain region corresponding to SEQ ID NO: 14.

In the invention, the anti-CD47 antibodies promote macrophage-mediated phagocytosis of a CD47-expressing cell.

In the invention, the anti-CD47 antibodies do not induce either an antibody-dependent cell-mediated cytotoxicity or an apoptosis activity.

In the invention, the antibody may comprise an IgG isotype selected from the group consisting of IgG 1 isotype and IgG2 isotype.

In the invention, the antibody may be prepared as an IgG4-reformatted CD47 antibody.

In one embodiment, the present invention provides a method for treating a cancer, comprising administering to a subject in need thereof a therapeutically effective amount of the anti-CD47 antibodies.

In one embodiment, the broad spectrum of mammalian cancers to be treated is selected from the group consisting of acute myeloid leukemia, chronic myeloid leukemia, acute lymphoblastic leukemia, non-Hodgkin's lymphoma, multiple myeloma, bladder cancer, breast cancer, head-and-neck squamous cell carcinoma, ovarian cancer, and colon cancer.

In further embodiment, the present invention provides a pharmaceutical composition comprising a therapeutically acceptable amount of the anti-CD47 antibodies and one or more pharmaceutically acceptable carriers. In particular, the pharmaceutical composition is effective in the treatment of a cancer.

In one embodiment of the present invention, TRB800-01, a research antibody Fab library, was screened with commercially available recombinant CD47 protein (R&D Systems, USA) to isolate fully human antibodies against CD47. TRB800-01 was constructed using blood samples collected from clinically diagnosed patients containing 16× oral, 22× esophageal, and 15× prostate cancers (IRB No. VGHKS17-CT11-13) with a capacity of ~1×10$^{10}$.

In another embodiment of the present invention, the titer of the eluted phages increased significantly through panning, indicating enrichment in CD47-specific binders. Randomly selected 384 clones from the 3rd-round panning was further confirmed using direct ELISA analysis against CD47 protein, and positive binders with OD$_{450}$ greater than 0.5 were selected for sequencing analysis. Seven unique clusters were identified and were chosen to be reformatted into full-length human IgG4 for expression using HEK293 cells in the FreeStyle™ 293-F system (Invitrogen, USA), and for further characterizations.

The present invention is further illustrated by the following examples, which should be construed as illustrative only and not in any way limit the remainder of the present invention. Without further illustration, it is believed that those skilled in the art will be able to make the best use of the present invention based on the description herein.

Example 1 Human Antibody Fab Library Screening Against Recombinant CD47 Protein

Human antibody Fab library was constructed from selected cancer patient bloods with diversity ~10$^{10}$. Briefly, the identification of CD47 antibodies from the antibody library was done as described below. ELISA well was coated with 500 ng/well (in PBS) of human CD47-Fc protein (R&D Systems, USA) for 16 hr at 4° C. After blocking, ~10$^{10}$ phages were added and incubated at room temperature for 1 hr on shaker. Unbound phages were removed and the wells were washed 10 times with PBS containing 0.05% Tween-20 (PBS-T). After washing, bound phages were eluted by adding 100 μl of 0.1M TEA solution (Sigma, USA) and neutralized with 50 μl of 1M Tris-HCl, pH7.4. Eluted phages were then used to infect log phase TG-1 cells, plated on 1.5% agar plates containing antibiotic and glucose, and incubated at 30° C. for overnight. On the next morning, scrapped bacteria (30 OD$_{600}$) were used for phage rescuing using M13 Hyperphages (PROGEN, Germany). After centrifugation, rescued phages were PEG-pelleted and reconstituted in PBS, titrated, and used for the next round of panning. The panning processes were repeated for two additional times. After final round of selection, individual clone was selected, grown, and induced with 1 mM IPTG for Fab productions. The supernatant containing expressed Fabs from each individual clone were analyzed by ELISA against CD47-Fc protein for binder identification.

Example 2 CD47 Binder Sequencing Analysis and Reformatting

ELISA positive binders with OD$_{450}$>0.5 were selected for sequencing analysis. Heavy chains of identified CD47 binders were engineered onto a human IgG4 scaffold to minimize recruitment of Fc-dependent effector functions such as ADCC and CDC. The amino acid sequences of the light chain and heavy chain variable (Vh) region, and the reformatted full length heavy chain sequences (in IgG4 isotype) of identified CD47 binders were listed in Table 1 and Table 2. Individual reformatted CD47 antibody heavy chain and corresponding light chain were then sub-cloned onto separate pCI-neo vector (Promega, USA) for pairwise HEK293 transfection, expression, purification, and characterization.

Example 3 Antibody Expression and Purification

HEK 293 cells and FreeStyle™ 293 Expression Medium (Invitrogen, USA) were used for recombinant antibody production. Transient transfection was done according to the manufacturer's instruction (Invitrogen, USA). To purify antibodies, the culture supernatant was applied to Pierce protein G agarose resin (ThermoFisher, USA) and were dialyzed against PBS. Purified antibody was analyzed by SDS-PAGE on 4-12% Bolt Bis-Tris plus gel (Invitrogen, USA) under reducing or non-reducing condition, and visualized by Coomassie brilliant blue staining (Invitrogen, USA).

Results from FIG. 1 showed all IgG4-reformatted anti-CD47 antibodies were properly expressed and formed. And also, greater than 90% purity of each individual antibody was obtained using Protein-G chromatography.

Example 4 CD47 Binding Study

To examine and confirm the binding specificity, purified anti-CD47 antibodies were firstly assayed using direct ELISA assay. Briefly, 96-well ELISA plate (Nunc, Denmark) was coated with 1 μg/ml of recombinant CD47-Fc or SIRP-α (R&D Systems, USA) for 16 hours at 4° C. CD47 or SIRP-α pre-coated wells were blocked with 5% non-fat milk in PBS at room temperature for 1 hr, and then 100 ul of 0.5 μg/ml human anti-CD47 antibodies were added and incubated for 1 hour at room temperature with shaking. After incubation and washes, 100 μl of 1:2500 diluted HRP-conjugated goat anti-human Fc antibody (Jackson ImmunoResearch, USA) were added to each well and incubated for 1 hour at room temperature. After final washing, bound antibodies were detected using TMB solution (Invitrogen, USA). The reaction was stopped by adding 50 μl of 1M HCl and read the absorbance of each well at $OD_{450}$ nm.

Figure 2A:
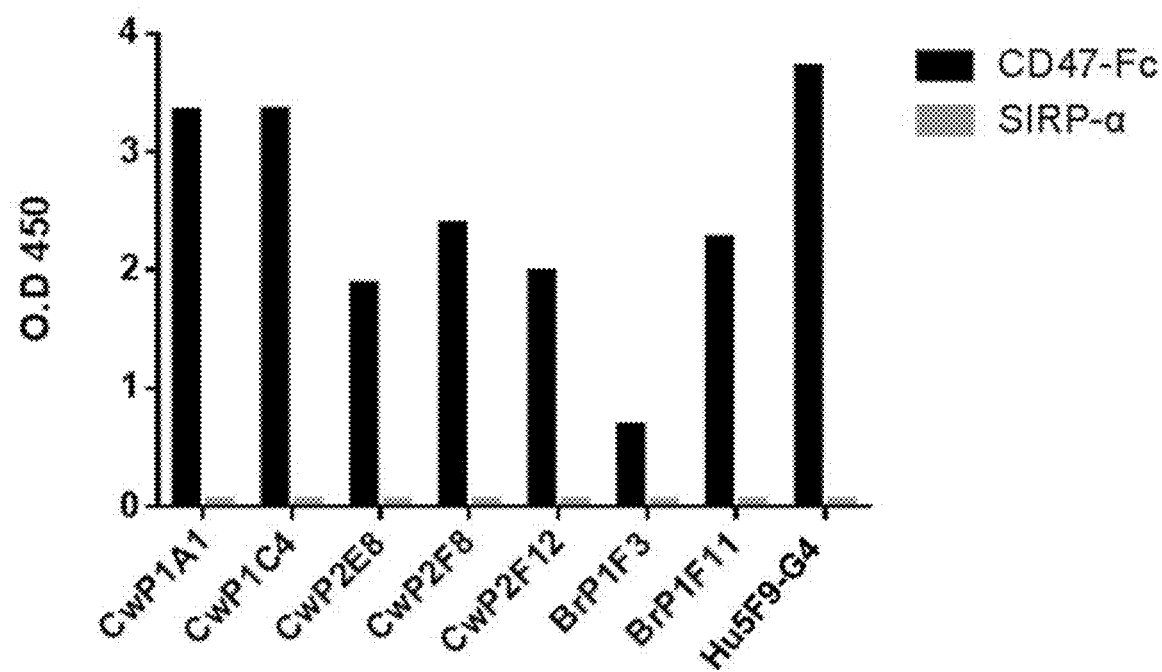
FIGS. 2A and 2B provide the results of the binding of the purified antibodies to CD47-Fc protein (R&D Systems, USA) using ELISA assay.

Results in FIG. 2A indicated all candidate antibodies and Hu5F9-G4, though binding activity varies among clones, were shown to be specific against recombinant CD47 with no cross-reactivity against SIRP-α protein (R&D Systems, USA). Hu5F9-G4, a humanized antibody targeting CD47 with extraordinary bioactivity in vitro and in vivo, was used as a positive control for comparison.

Titration ELISA assay was used to examine the binding activity of these candidate antibodies. For titration ELISA assay, wells were coated with 1 μg/ml of recombinant CD47-Fc for 16 hr at 4° C. CD47 precoated wells were blocked with 5% non-fat milk in PBS at room temperature for 1 hr, and then 100 ul 1:3 serial diluted anti-CD47 antibody starting from 30 nM were added and incubated for 1 hour at room temperature with shaking. After incubation and washes, 100 ul of 1:2500 diluted HRP-conjugated goat anti-human Fc antibody (Jackson ImmunoResearch, USA) were added to each well and incubated for 1 hour at room temperature. After final washing, bound antibodies were detected using TMB solution (Invitrogen, USA). The reaction was stopped with 1M HCl and read the absorbance of each well at $OD_{450}$ nm. $EC_{50}$, the antibody concentration required for half of max absorbance, was then calculated by GraphPad Software for each tested CD47 antibody.

Figure 2B:
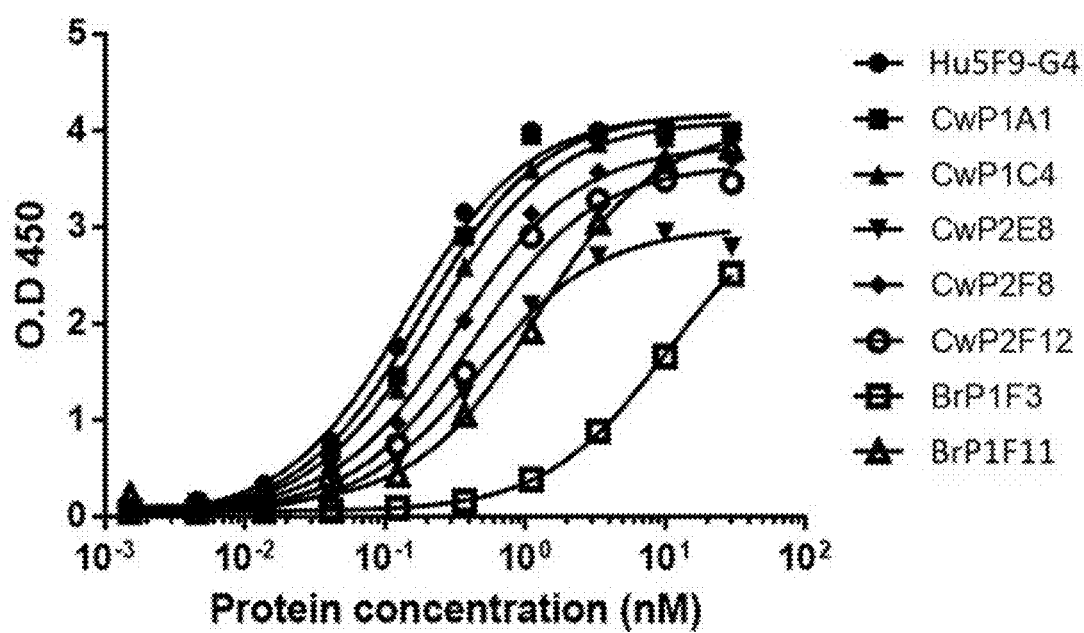

As shown in FIG. 2B, all tested Anti-CD47 antibodies bound to recombinant CD47 in a dose-dependent manner, and the measured $EC_{50}$ for Hu5F9-G4, CwP1A1, CwP1C4, CwP2E8, CwP2F8, CwP2F12, BrP1F3, and BrP1F11 were 0.1442 nM, 0.1835 nM, 0.2271 nM, 0.4694 nM, 0.3264 nM, 0.4413 nM, 10.1 nM, and 1.21 nM, respectively.

Example 5 Cell Surface Antigen-Binding Assay

In one embodiment of the invention, Cell surface CD47 binding by flow cytometer was used to examine if discrepancies between recombinant and natural CD47 protein. The binding activity with increasing concentrations of the Anti-CD47 antibodies against cell-surface CD47 on Jurkat-1 or HL-60 cells (BCRC, Taiwan). For cell surface antigen-binding assay, $1 \times 10^5$ of Jurkat-1 cells (BCRC, Taiwan) were incubated with 0.001, 0.01, 0.1, 1, 10, or 100 μl/ml of anti-CD47 antibody in 100 μL at 4° C. for 15 min. After incubation, the cells were washed with ice-cold staining ($1 \times PBS + 2\%$ $FBS + 0.05\%$ $NaN_3$) buffer for three times, followed by incubation with FITC-conjugated goat anti-human Fc antibody (Jackson ImmunoResearch, USA). Lastly, cells were washed and analyzed using BD Accuri™ C6 Plus flow cytometer (BD Biosciences, USA). Mean fluorescence intensity (MFI) values were plotted.

Figure 3A:
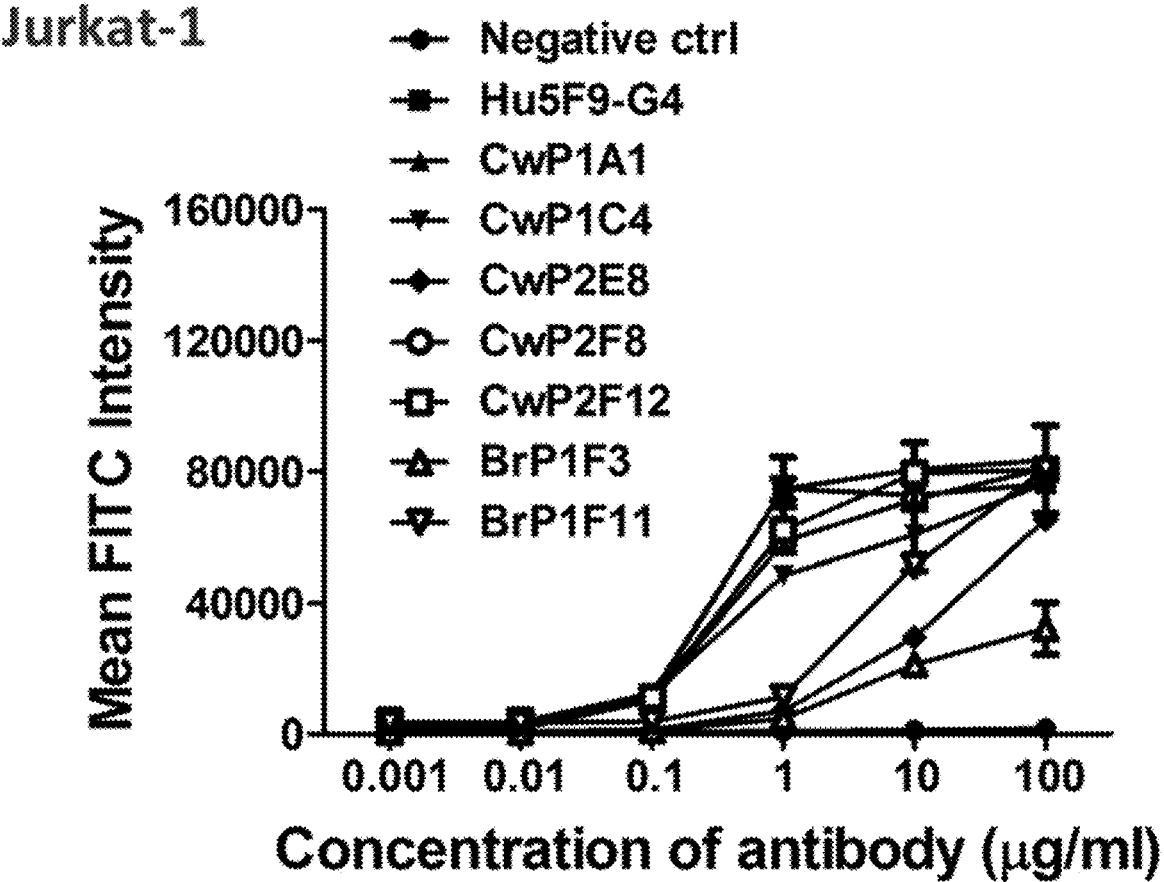
FIGS. 3A and 3B show the flow cytometry analysis of cell-surface CD47 binding using the anti-CD47 antibodies; wherein the anti-CD47 antibodies from library bound to cell-surface CD47 in a dose-dependent manner as analyzed using flow cytometry; and Jurkat-1 cells (FIG. 3A) or HL-60 cells (FIG. 3B) were stained with the anti-CD47 antibodies, Hu5F9-G4 antibody, or purified human IgG4 isotype control and analyzed for surface binding by flow cytometry, and FITC-conjugated goat anti-human Fc antibody (Jackson ImmunoResearch, USA) was used for detection.
Figure 3B:
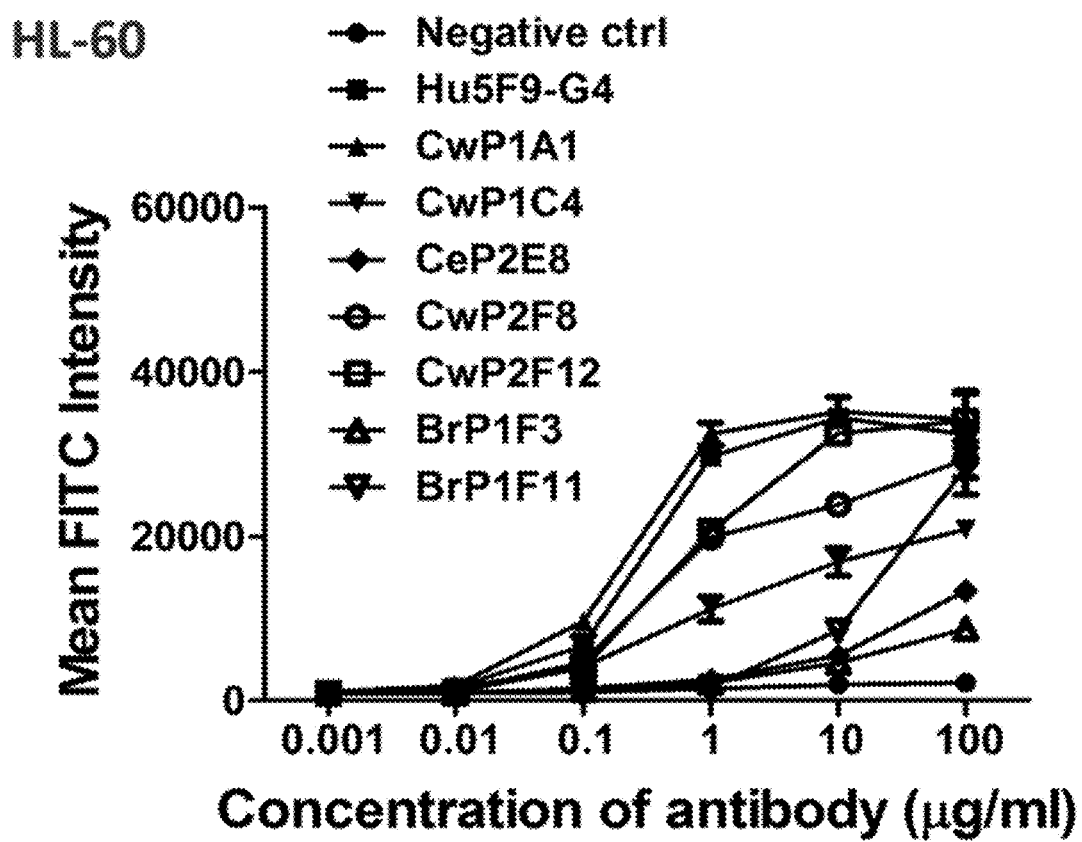

The results collected from FIGS. 3A and 3B suggested a dose-dependent manner on cell surface binding of the anti-CD47 antibodies and Hu5F9-G4, but not the human IgG4 isotype control (BioLegend, USA), on both tested cell lines.

Example 6 Competition Assay of CD47 Binding Using Flow Cytometry

In another embodiment of the invention, the binding specificity of the anti-CD47 antibodies against natural CD47 was performed by antibody binding competition assay using flow cytometry with or without excess amount of recombinant CD47-Fc protein was performed. $1 \times 10^5$ of Jurkat-1 cells were incubated with 1 μg/ml of human anti-CD47 antibody in the absence or presence of 10 μg/ml recombinant CD47-Fc protein at 4° C. for 15 minutes. After that, the cells were washed and stained with FITC conjugated goat anti-human Fc antibody (Jackson ImmunoResearch, USA) before analyzed using BD Accuri™ C6 Plus (BD Biosciences, USA) flow cytometer.

Figure 4:
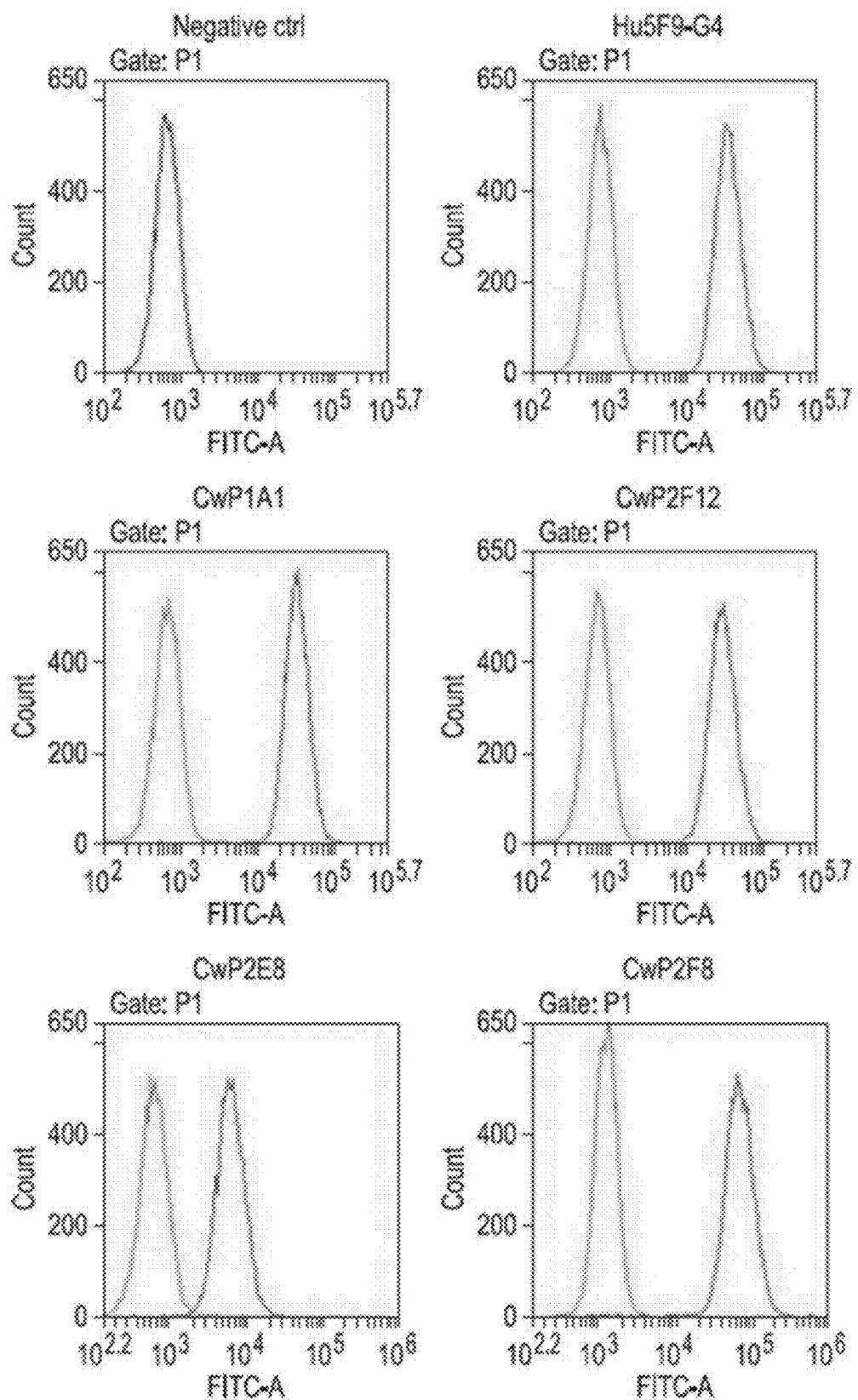
FIG. 4 shows the competition analysis of antibody binding between cell-surface CD47 and recombinant CD47-Fc protein using flow cytometer; wherein Jurkat-1 cells were stained with the anti-CD47 antibodies (1 μg/ml) in the absence (right peak) or presence (left peak) of 20 μg/ml CD47-Fc fusion proteins and analyzed for surface binding using flow cytometry; and FITC-conjugated goat anti-human Fc antibody (Jackson ImmunoResearch, USA) was used for detection. Hu5F9-G4 was included for comparison and purified human IgG4 was used as negative control (upper left panel). A representative flow analysis was shown using selected CD47 antibodies, Hu5F9-G4, or a human IgG4 isotype control.

FIG. 4 shows that surface CD47 binding activity of the anti-CD47 antibodies and Hu5F9-G4 were shown to be blocked by the presence of 10 μg/ml of CD47-Fc fusion proteins, indicating the specific binding of the all tested antibodies against CD47

Example 7 the CD47-SIRP-α Interaction Blocking Assay

The CD47-SIRPα interaction blocking activities of recombinant anti-CD47 antibodies were tested using ELISA assay. ELISA wells (Nunc, Denmark) were coated with 1 μg/ml of recombinant human His-tagged SIRP-α protein (R&D Systems, USA) for 16 hr at 4° C. After blocking, 1 μg/ml of recombinant CD47-Fc protein and 3-fold serially diluted of anti-CD47 antibody starting from 30 nM were added and incubated at room temperature for 1 hr. After incubation, wells were washed and incubated with HRP-conjugated goat anti-human Fc antibody (1:2500 dilution, Jackson ImmunoResearch, USA) for 1 hr. After final washing, the bound CD47-Fc proteins were detected with TMB substrate. The reaction was stopped by adding 1M HCl and OD450 readings were obtained. $IC_{50}$, the antibody concentration required to inhibit half of max absorbance, was calculated by GraphPad Software for each tested CD47 antibody.

Figure 5:
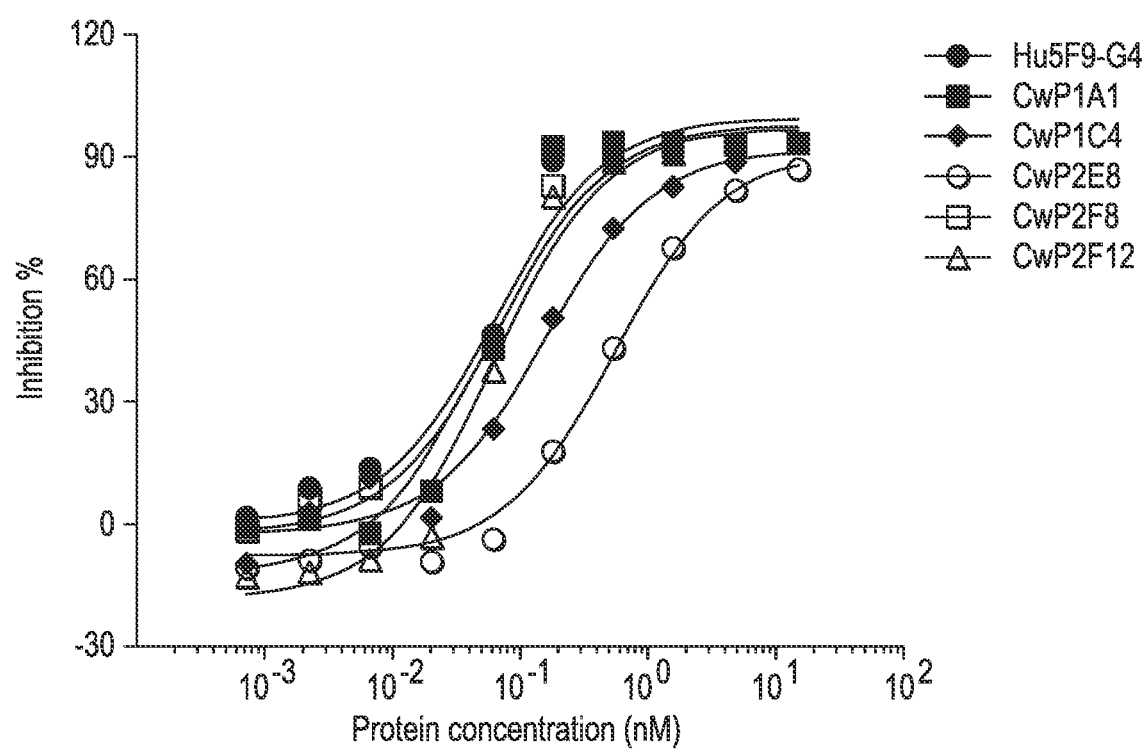
FIG. 5 shows the blockage of CD47-SIRP-α interaction by the anti-CD47 antibodies. Human CD47-Fc binding to SIRP-α pre-coated wells was detected by ELISA in the absence or presence of increasing concentrations of the anti-CD47 antibodies or Hu5F9-G4 as control. The anti-CD47 antibodies and Hu5F9-G4, with different degree of activities, could block the interaction of CD47 with SIRP-α.

The anti-CD47 antibodies as shown in FIG. 5 were able to block the interaction between recombinant human CD47 and recombinant human SIRP-α. The calculated $IC_{50}$s for Hu5F9-G4, CwP1A1, CwP1C4, CwP2E8, CwP2F8 and CwP2F12 is 0.063 nM, 0.053 nM, 0.155 nM, 0.556 nM, 0.068 nM and 0.063 nM, respectively. Results from this study indicated CwP1A1, CwP2F8 and CwP2F12 have similar or even better blocking activities than that of Hu5F9-G4.

Example 8 In Vitro Antibody-Mediated Phagocytosis Assay

Whether the CD47 and SIRP-α interaction blocking antibodies could induce macrophage-mediated phagocytosis of $CD47^+$ cancer cells were then examined. In vitro phagocytosis assays were done as described below briefly. The differentiation of THP-1 (BCRC, Taiwan) monocytes to macrophages was induced by PMA, LPS (Sigma, USA) and IFN-γ (R&D Systems, USA). The polarized THP-1 cells were then stained with CellTracker Red (CTR, Life Technology, USA) before use. CFSE-labeled human cells, Jurkat-1 or HL-60 cells (BCRC, Taiwan), in the presence of 5 μg/ml isotype control antibody, Hu5F9-G4, or human anti-CD47 antibodies (IgG4) were incubated with polarized THP-1 macrophages for 3 hr at 37° C. Cells were washed before analyzed by flow cytometry to determine the phagocytic index (number of cells ingested per 100 macrophages). PBMC-derived macrophages were induced by 50 ng/ml rhM-CSF (Peprotech, USA) treatment for 7 days and confirmed by anti-CD14 antibody (Abcam, USA) staining. CFSE-labeled HL-60 cells in the presence of 10 ng/ml isotype control antibody, Hu5F9-G4, or human anti-CD47 antibodies were incubated with macrophages for 2 hr at 37° C. Then, the cells were analyzed by flow cytometry to determine the phagocytic index.

Figure 6A:
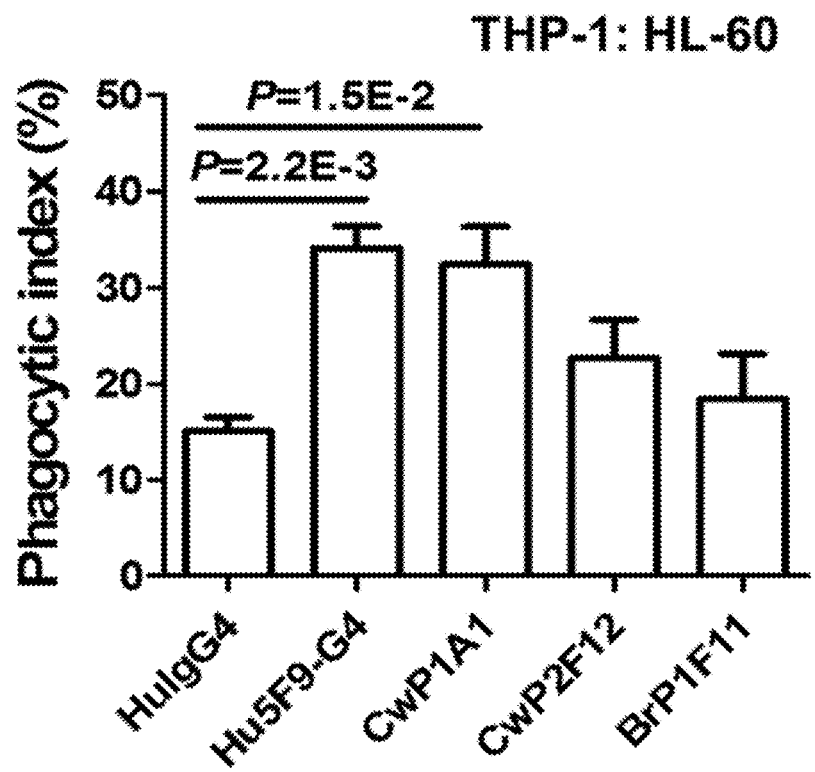
FIGS. 6A-6C show the anti-CD47 antibodies enhanced antibody-dependent phagocytosis activities of HL-60 or Jurkat-1 cells using polarized THP-1 macrophages or PBMC. The anti-CD47 antibodies, CwP1A1, CwP2E8, BrP1F3, BrP1F11, and Hu5F9-G4 were able to enhance, significantly, polarized THP-1- or PBMC-mediated phagocytosis against antibody-treated cells.
Figure 6B:
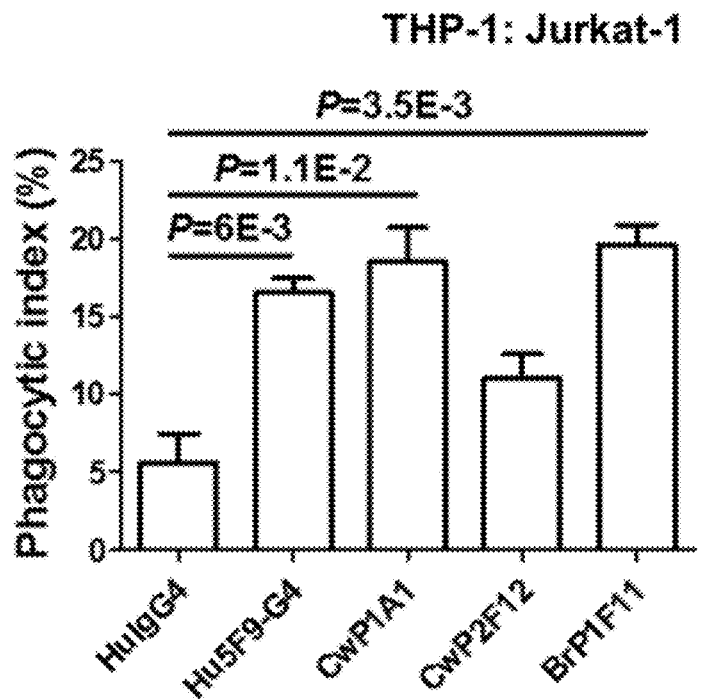
Figure 6C:
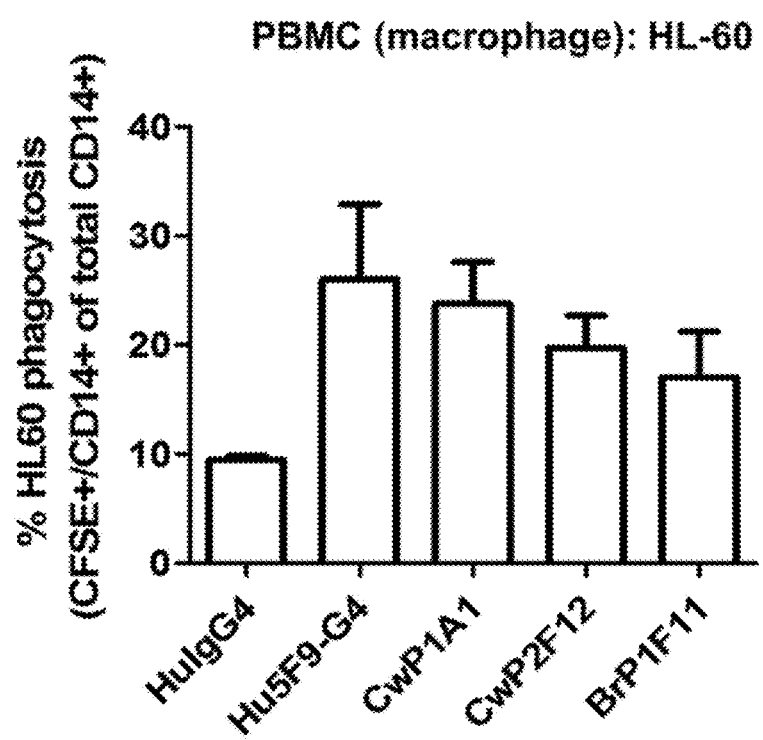

The HL-60 AML and Jurkat-1 ALL cells were used as target cells. Polarized THP-1 cells as well as human peripheral blood-derived macrophages were used to examine the phagocytotic activity. Phagocytic activity was measured by flow cytometry. As shown in FIGS. 6A-C, human anti-CD47 antibodies and Hu5F9-G4 significantly promoted phagocytosis of tumor cells by polarized THP-1 and PBMC-derived macrophages.

Example 9 ADCC Assay

To evaluate if human CD47 antibodies also enable ADCC in addition to phagocytosis, CwP1A1-IgG4, BrP1F11-IgG4, and Hu5F9-G4 with IgG4 scaffold were examined for their ADCC activities using an ADCC reporter bioassay. In this study, CwP1A1-IgG1 with a human IgG1 Fc fragment and HuIgG4 were also included as controls, respectively. The ADCC Reporter Bioassay Complete Kit (Promega. USA) with Raji cells as target was used according to the manufacturer's instructions. Six to one ratio of effector-to-target cells were incubated with. HuIgG4, Hu5F9-G4, CwP1A1-IgG4, CwP1A1-IgG4, or BrP1F11-IgG4 at different concentrations as indicated (x-axis) for 6 hours. After incubation, Bio-Glo luciferase assay reagent was added and luminescence was read. Samples were run in duplicate and averages of the duplicate values were graphed with error bars displaying standard error of the mean (SEM).

Figure 7:
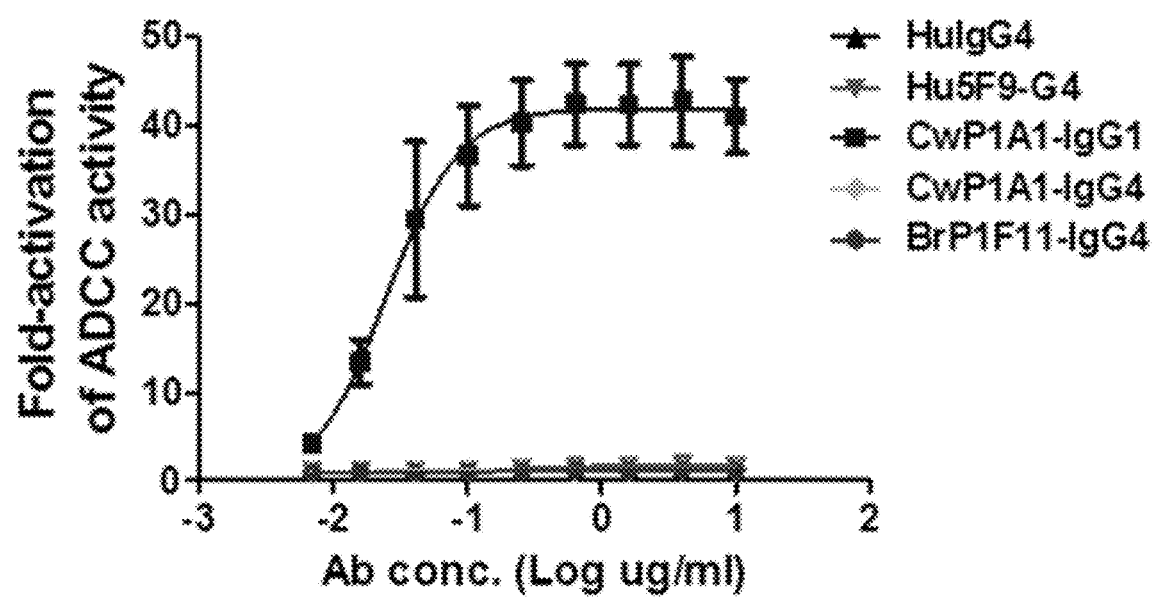
FIG. 7 shows the anti-CD47 antibodies did not induce ADCC. The ADCC Reporter Bioassay Complete Kit (Promega, USA) with Raji cells as target was used. Six to one ratio of effector-to-target cells were incubated with Hu5F9-G4, CwP1A1-IgG4, or BrP1F11-IgG4 at different concentrations as indicated (x-axis) for 6 hours. CwP1A1-IgG1 with a human IgG1 Fc fragment and HuIgG4 were also included as controls.

Results shown in FIG. 7 indicated CwP1A1-IgG1 is able to induce an ADCC activity in a dose-dependent manner. In contrast, CwP1A1-IgG4, BrP1F11-IgG4, Hu5F9-G4, and HuIgG4 did not induce ADCC. Collectively, the mechanism of action of TRB human CD47 antibodies, CwP1A1-IgG4 and BrP1F11-IgG4, do not induce either ADCC or apoptosis, but rather activation of antibody-dependent cellular phagocytosis.

Example 10 Apoptosis Assay

Apoptosis assay was carried out to examine if the binding of the anti-CD47 antibodies to CD47 directly induce apoptosis of cancer cells. Human cells, Jurkat-1, HL-60, or Raji cells, were resuspended at $1 \times 10^6$ cells/ml in RPMI-1640 medium containing 10% FBS. 10 μg/ml isotype control, 2D3, Hu5F9-G4, or human anti-CD47 antibodies (IgG4) were added and the cells were incubated at 37° C. for 3 hr. In the case of HL-60 cell line, staurosporine was used as a positive control. Apoptotic cells were identified by staining with Annexin-V and PI according to the manufacturer's instructions (BD Biosciences, USA) and analyzed using flow cytometry.

Figure 8A:
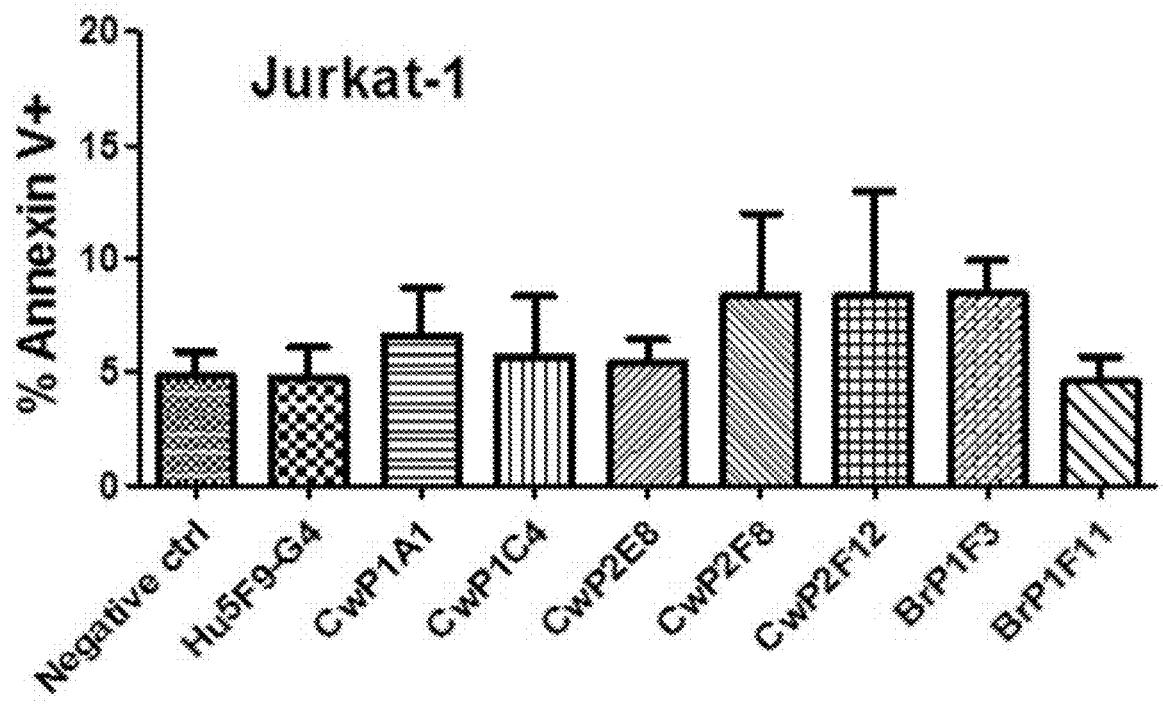
FIGS. 8A and 8B show apoptosis assay of Jurkat-1 or HL-60 cells in the presence of the anti-CD47 antibodies. Cells were incubated with 10 ug/ml of the anti-CD47 antibodies, Hu5F9-G4, or IgG4 isotype control. Apoptotic cells were identified by staining with Annexin-V and analyzed using flow cytometry. The anti-CD47 antibodies or Hu5F9-G4 treatment did not induce apoptosis of Jurkat-1 (FIG. 8A) or HL-60 cells (FIG. 8B).
Figure 8B:
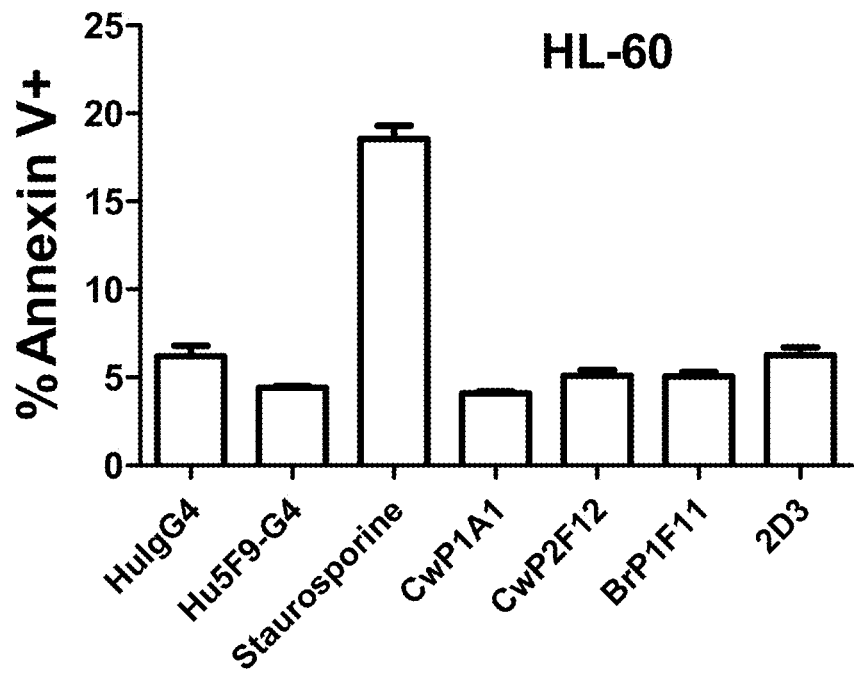

As shown in FIG. 8A, it is found that as similar to the isotype control, the tested anti-CD47 antibodies and Hu5F9-G4 did not induce apoptosis of Jurkat-1 cells. FIG. 8B showed that human anti-CD47 antibodies, unlike treatment with staurosporine, did not induce apoptosis of HL-60 cells. Similar results also obtained using Raji cells for assay (data not shown). Collectively, our results indicated anti-human CD47 antibodies induce phagocytosis rather than apoptosis activity.

The anti-CD47 antibodies with therapeutic potentials in this invention are currently tested in xenograft animal models for their efficacies against acute myeloid leukemia and solid tumors.

Example 11 RBC Surface Antigen-Binding Assay and RBC Aggregation Assay

For RBC surface antigen-binding assay, cell surface CD47 binding activity was measured using flow cytometer. Human red blood cells were isolated by Ficoll-Paque Plus (Sigma, Sweden) using density gradient centrifugation. Purified human RBCs were incubated with 1, 10 and 100 μg/ml of anti-CD47 antibodies (IgG4) in 100 μl at 4° C. for 15 min. After incubation, the cells were washed with ice-cold staining buffer (1×PBS+2% FBS+0.05% $NaN_3$) for three times, followed by incubation with FITC-conjugated goat anti-human Fc antibody (Jackson ImmunoResearch, USA). Cells were washed and analyzed using BD Accuri™ C6 Plus flow cytometer (BD Biosciences, USA). Mean fluorescence intensity (MFI) values were plotted. For RBC aggregation assay, human RBCs were first diluted in PBS and then added to a 96-well round bottom plate (Thermo, Denmark) with various concentrations of antibodies. The plate was incubated at 37° C. for 4 h. Non-hemagglutinated RBCs were defined as punctuate dot, and the HA index was calculated by Image J software.

Figure 9A:
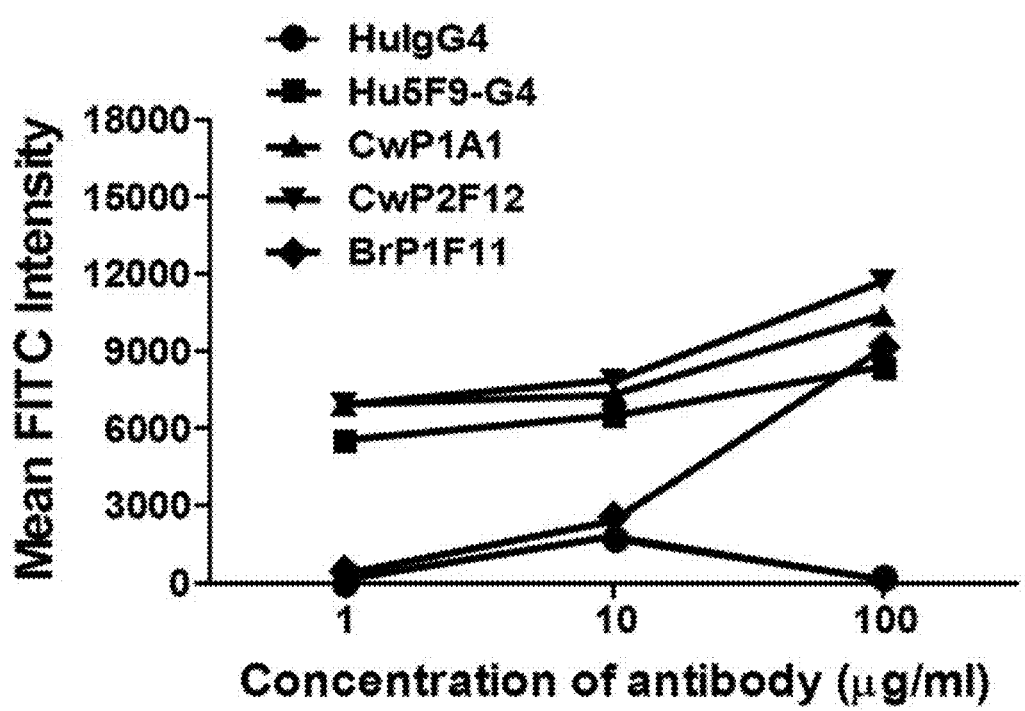
FIG. 9A shows RBC surface antigen-binding assay and FIG. 9B shows RBC aggregation assay. Human anti-CD47 antibodies (CwP1A1, CwP2F12 and BrP1F11) bound to surface CD47 of RBCs in a dose-dependent manner. Further, CwP1A1 and BrP1F11 did not induce hemagglutination of human RBCs.
Figure 9B:
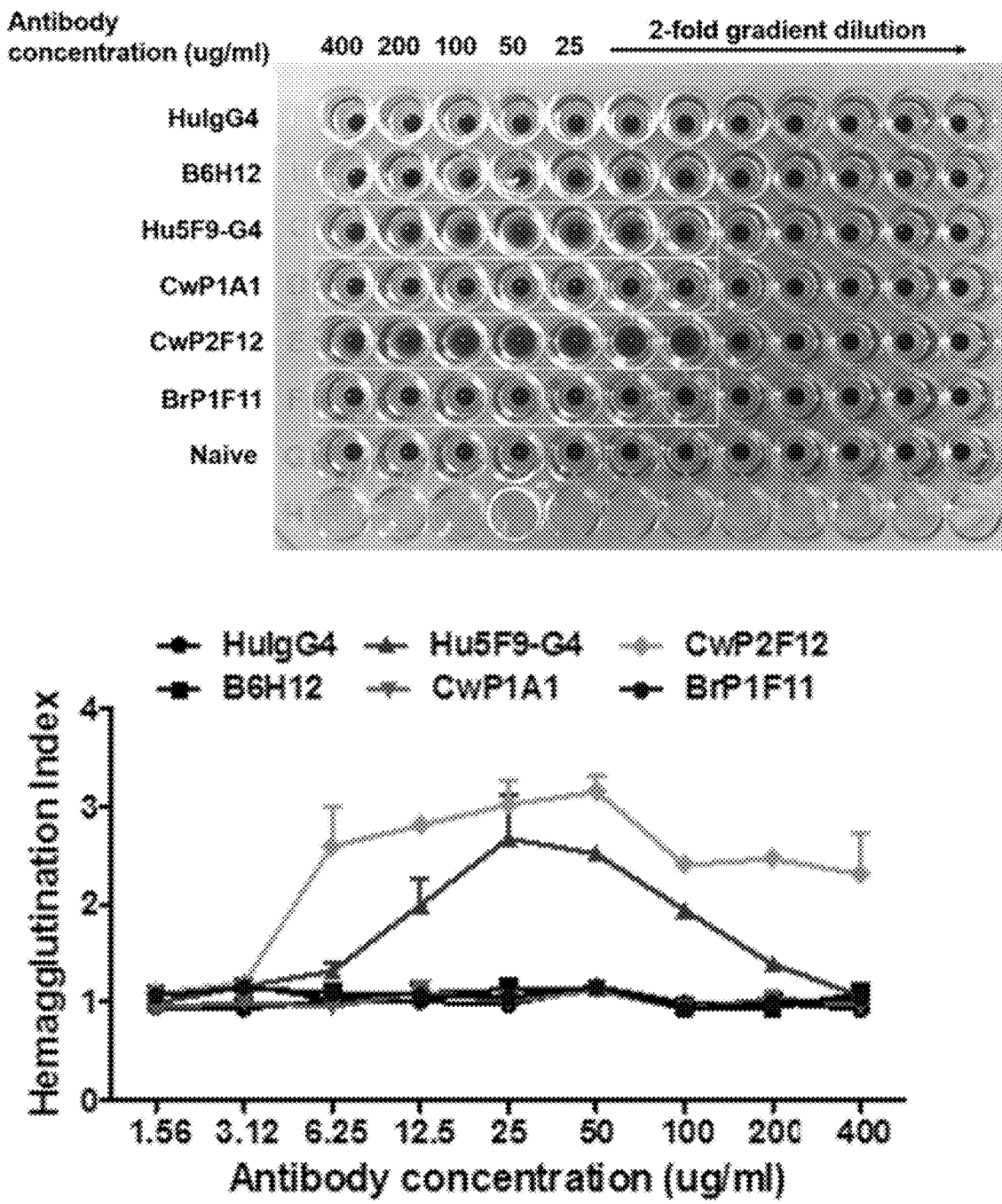

As shown in FIG. 9A, human anti-CD47 antibodies (CwP1A1, CwP2F12 and BrP1F11) bound to surface CD47 of RBCs in a dose-dependent manner. FIG. 9B showed CwP1A1 and BrP1F11 did not induce hemagglutination of human RBCs. On the contrary, Hu5F9-G4, an anti-CD47 antibody under clinical investigations, induced serious RBC hemagglutination. Results indicated, anti-CD47 antibodies, CwP1A1 and BrP1F11, could have better safety profile than that of Hu5F9-G4 regards to the hemagglutination of RBCs.

Example 12 In Vivo Anti-CD47 Antibody Efficacy Evaluation Using Mouse Xenograft Model Male SCID mice (BioLASCO, Taiwan) were injected s.c. in the right flank with 100 μl Matrigel (Corning, USA) plus $1.0 \times 10^7$ HL-60 cells (0.1 mL cell suspension). Mice were intraperitoneally injected with isotype control antibody (400 ug/mouse), Hu5F9-G4, or human anti-CD47 antibodies, BrP1F11-G4 and CwP1A1 in IgG1 or IgG4 isotype (400 μg/mouse) three times per week for three weeks. Tumor volumes were measured twice per week. Tumor volumes were calculated using formula $V=LW^2/2$. After sacrificed, tumor tissues were resected and fixed with formalin.

Figure 10A:
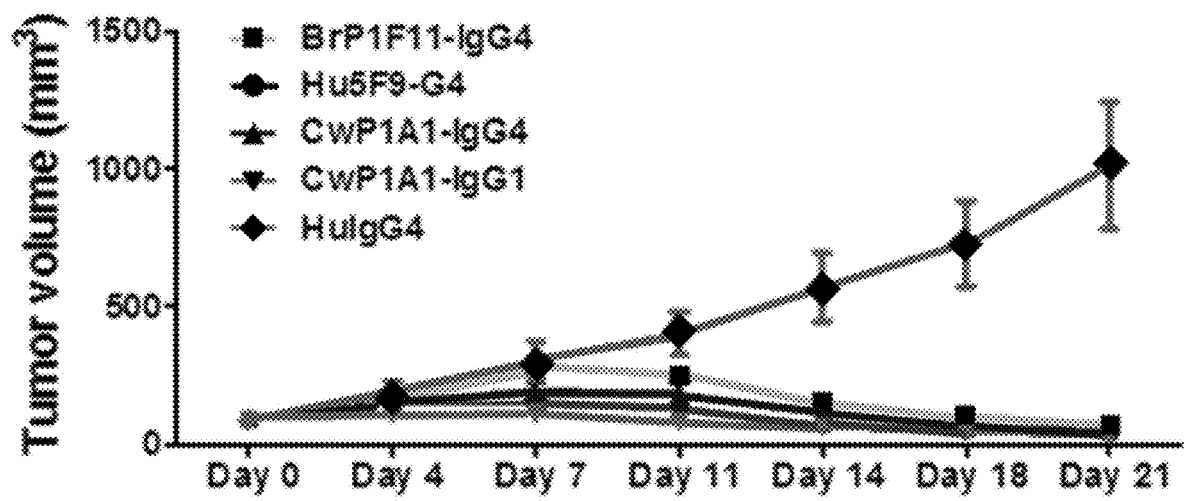
FIGS. 10A and 10B show anti-tumor activities with human anti-CD47 antibodies, CwP1A1 and BrP1F11, in HL-60 mouse xenograft model. Male SCID mice were injected s.c. in the right flank with 100 μl Matrigel plus $1.0 \times 10^7$ HL-60 cells, and then isotype control antibody (400 μg/mouse), Hu5F9-G4, or human anti-CD47 antibodies, BrP1F11-G4 and CwP1A1 in IgG1 or IgG4 isotype (400 μg/mouse) were injected i.p. three times per week for three weeks. CwP1A1-G1, CwP1A1-G4 and BrP1F11-G4 antibodies exhibited significant antitumor activity against the HL60 xenograft.
Figure 10B:
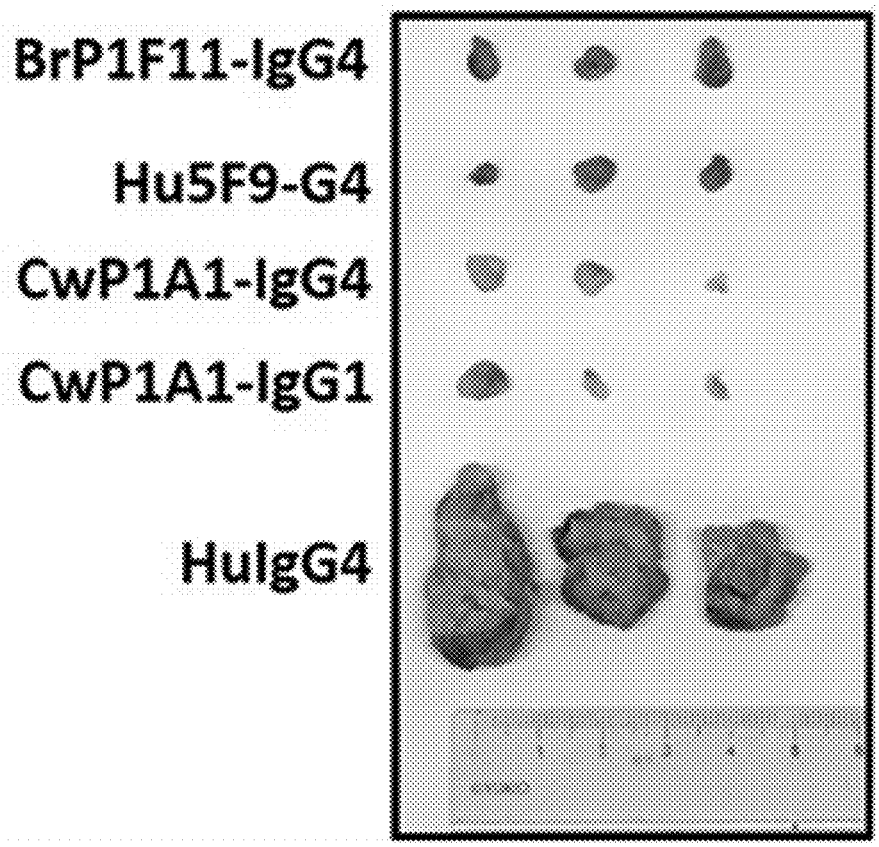

To evaluate the anti-tumor activities, anti-CD47 antibodies, BrP1F11-G4, CwP1A1-G1 and CwP1A1-G4 were tested using HL-60 xenograft model and were compared with Hu5F9-G4 antibody. As shown in FIG. 10A, CwP1A1-G1, CwP1A1-G4 and BrP1F11-G4 antibodies administered intraperitoneally at 400 μg/mouse demonstrated significant antitumor activity against the human acute promyelocytic leukemia HL60 xenograft and which is comparable to that of Hu5F9-G4. Representative tumors from each treatment were shown in FIG. 10B.

Example 12 Pharmacokinetics Assessment

The PK of the anti-CD47 antibody will be evaluated in rats (n=5). By tail vein injection, 10 mg/kg the anti-CD47 antibodies will be administered into rat. Blood samples will be collected from each rat via the caudal vena cava at 0 min, 1 h, 4 h, 8 h, 12 h, 1 day, 2 days, 3 days, 4 days, 6 days, 8 days, 10 days, 12 days and 14 days after the injection. The concentration of antibody in serum will be determined by enzyme-linked immunosorbent assay (ELISA). Serum concentrations of the anti-CD47 antibody were interpolated from a 4-parameter logistic regression of the standard curve on the same plate.

Given the above, the anti-CD47 antibodies were engineered on a human IgG4 scaffold to minimize recruitment of Fc-dependent effector functions (ADCC and CDC), and did not involve apoptosis, and therefore, it is suggested in the invention that the anti-CD47 antibodies (and so does Hu5F9-G4) is able to initiate an activation of macrophage-mediated phagocytosis through blocking the interaction of CD47 with SIRP-α.

---

What is claimed is:

1. An isolated human anti-CD47 antibody, or an antigen-binding fragment thereof, comprising:
   (a) a reformatted heavy chain region comprising an amino acid sequence of SEQ ID NO: 15 and a light chain region having an amino acid sequence of SEQ ID NO: 2;
   (b) a reformatted heavy chain region comprising an amino acid sequence of SEQ ID NO: 16 and a light chain region having an amino acid sequence of SEQ ID NO: 4;
   (c) a reformatted heavy chain region comprising an amino acid sequence of SEQ ID NO: 17 and a light chain region having an amino acid sequence of SEQ ID NO: 6;
   (d) a reformatted heavy chain region comprising an amino acid sequence of SEQ ID NO: 18 and a light chain region having an amino acid sequence of SEQ ID NO: 8;
   (e) a reformatted heavy chain region comprising an amino acid sequence of SEQ ID NO: 19 and a light chain region having an amino acid sequence of SEQ ID NO: 10;
   (f) a reformatted heavy chain region comprising an amino acid sequence of SEQ ID NO: 20 and a light chain region having an amino acid sequence of SEQ ID NO: 12; or
   (g) a reformatted heavy chain region comprising an amino acid sequence of SEQ ID NO: 21 and a light chain region having an amino acid sequence of SEQ ID NO: 14.

2. The antibody or antigen-binding fragment of claim 1, wherein the antibody or antigen-binding fragment thereof blocks the interaction of CD47 with signal-regulatory protein alpha (SIRP-α).

3. The antibody or antigen-binding fragment of claim 1, wherein the antibody or antigen-binding fragment promotes or enhances at least one effect selected from the group consisting of: enhancing macrophage-mediated phagocytosis, not inducing antibody-dependent cell-mediated cytotoxicity, not inducing apoptosis, and not inducing hemagglutination of human RBCs.

4. The antibody or antigen-binding fragment of claim 1, which promotes macrophage-mediated phagocytosis of a CD47-expressing cell.

5. A method of treating a CD47-expressing cancer in a subject in need thereof, comprising
   administering to said subject a therapeutically effective amount of the antibody or antigen-binding fragment of claim 1, wherein the cancer is selected from the group consisting of acute myeloid leukemia, chronic myeloid leukemia, acute lymphoblastic leukemia, non-Hodgkin's lymphoma, multiple myeloma, bladder cancer, breast cancer, head-and-neck squamous cell carcinoma, ovarian cancer, and colon cancer.

6. A pharmaceutical composition comprising
   the antibody or antigen-binding fragment that binds human CD47 as set forth in claim 1, and a pharmaceutically acceptable carrier and/or excipient.

* * * * *